United States Patent
Komori et al.

(10) Patent No.: US 8,962,158 B2
(45) Date of Patent: Feb. 24, 2015

(54) MATERIAL HAVING INDOLOCARBAZOLE COMPOUND FOR PHOSPHORESCENT LIGHT-EMITTING ELEMENT AND ORGANIC ELECTROLUMINESCENT ELEMENT USING THE SAME

(75) Inventors: Masaki Komori, Kitakyushu (JP); Takahiro Kai, Kitakyushu (JP); Toshihiro Yamamoto, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 158 days.

(21) Appl. No.: 13/256,363

(22) PCT Filed: Mar. 25, 2010

(86) PCT No.: PCT/JP2010/055223
§ 371 (c)(1),
(2), (4) Date: Sep. 13, 2011

(87) PCT Pub. No.: WO2010/113755
PCT Pub. Date: Oct. 7, 2010

(65) Prior Publication Data
US 2012/0001165 A1 Jan. 5, 2012

(30) Foreign Application Priority Data
Mar. 31, 2009 (JP) .................................. 2009-085638

(51) Int. Cl.
H01L 51/54 (2006.01)
C07D 487/04 (2006.01)
C07D 403/14 (2006.01)
C09K 11/06 (2006.01)
H01L 51/00 (2006.01)
H05B 33/14 (2006.01)
H01L 51/50 (2006.01)

(52) U.S. Cl.
CPC ............ *C07D 487/04* (2013.01); *C07D 403/14* (2013.01); *C09K 11/06* (2013.01); *H01L 51/0072* (2013.01); *H05B 33/14* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *H01L 51/0058* (2013.01); *H01L 51/5016* (2013.01); *Y10S 428/917* (2013.01)
USPC ............. 428/690; 428/917; 313/504; 257/40; 257/E51.024; 548/418; 546/276.7; 546/256; 544/212; 544/296; 544/102; 544/37

(58) Field of Classification Search
None
See application file for complete search history.

(56) References Cited

U.S. PATENT DOCUMENTS

| | | | |
|---|---|---|---|
| 2009/0309488 A1* | 12/2009 | Kato et al. ..................... | 313/504 |
| 2010/0012931 A1 | 1/2010 | Kato et al. | |
| 2010/0187977 A1 | 7/2010 | Kai et al. | |
| 2011/0037062 A1 | 2/2011 | Fukumatsu et al. | |
| 2011/0062429 A1 | 3/2011 | Kai et al. | |
| 2012/0235133 A1 | 9/2012 | Kai et al. | |

FOREIGN PATENT DOCUMENTS

| | | |
|---|---|---|
| EP | 0 908 787 A2 | 4/1999 |
| WO | WO 2008/056746 A1 | 5/2008 |
| WO | WO 2009/116377 A1 | 9/2009 |
| WO | WO 2009/136595 A1 | 11/2009 |

(Continued)

OTHER PUBLICATIONS

English translation of International Preliminary Report on Patentability issued Nov. 17, 2011, in PCT International Application No. PCT/JP2010/055223.
International Search Report for PCT/JP2010/055223 dated Jun. 29, 2010.

(Continued)

*Primary Examiner* — Andrew K Bohaty
(74) *Attorney, Agent, or Firm* — Birch, Stewart, Kolasch & Birch, LLP

(57) ABSTRACT

Provided is an organic electroluminescent device (organic EL device), which has improved luminous efficiency, has sufficient driving stability, and has a simple construction. The organic EL device of the present invention is an organic electroluminescent device, including a light-emitting layer and a hole-transporting layer between an anode and a cathode laminated on a substrate, in which the light-emitting layer contains a phosphorescent light-emitting dopant and an indolocarbazole compound that serves as a host material, or alternatively, the hole-transporting layer contains an indolocarbazole compound. The indolocarbazole compound is represented by the following formula (1). In the formula: $A_1$'s each represent an aromatic hydrocarbon group or an aromatic heterocyclic group, provided that at least one of $A_1$'s has a fused ring structure; and $R_1$'s each represent a hydrogen atom, an alkyl group, an alkoxy group, or an acyl group.

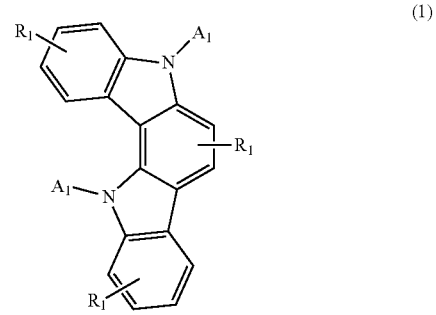

6 Claims, 2 Drawing Sheets

(56) References Cited

FOREIGN PATENT DOCUMENTS

| | | |
|---|---|---|
| WO | WO 2009/148062 A1 | 12/2009 |
| WO | WO 2011/080972 A1 | 7/2011 |

OTHER PUBLICATIONS

Extended European Search Report issued Jul. 26, 2012, in European Patent Application No. 10758528.3.

* cited by examiner

MATERIAL HAVING INDOLOCARBAZOLE COMPOUND FOR PHOSPHORESCENT LIGHT-EMITTING ELEMENT AND ORGANIC ELECTROLUMINESCENT ELEMENT USING THE SAME

TECHNICAL FIELD

The present invention relates to a material for a phosphorescent light-emitting device for an organic electroluminescent device and an organic electroluminescent device using the material, and more specifically, to a thin-film-type device which emits light when an electric field is applied to a light-emitting layer formed of an organic compound.

BACKGROUND ART

In general, an organic electroluminescent device (hereinafter, referred to as organic EL device) is constructed of a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine compound and a light-emitting layer formed of an 8-hydroxyquinoline aluminum complex (hereinafter, referred to as Alq3) are provided between two electrodes as thin films, resulting in a significant improvement in luminous efficiency, compared with conventional devices in which a single crystal of anthracene molecules or the like is used. Thus, the development of the above-mentioned organic EL device has been promoted in order to accomplish its practical application to a high-performance flat panel having features such as self luminescence and rapid response.

Further, studies have been made on using phosphorescent light rather than fluorescent light as an attempt to raise the luminous efficiency of a device. Many kinds of devices including the above-mentioned device in which a hole-transporting layer formed of an aromatic diamine compound and a light-emitting layer formed of Alq3 are provided emit light by using fluorescent light emission. However, by using phosphorescent light emission, that is, by using light emission from a triplet excited state, luminous efficiency is expected to be improved by about three times to four times, compared with the case of using conventional devices in which fluorescent light (singlet) is used. In order to accomplish this purpose, studies have been made on adopting a coumarin compound or a benzophenone compound as a light-emitting layer, but extremely low luminance has only been provided. Further, studies have been made on using a europium complex as an attempt to use a triplet state, but highly efficient light emission has not been accomplished. In recent years, many studies centered on an organic metal complex such as an iridium complex have been made, as described in Patent Literature 1, for the purpose of attaining the high efficiency and long service life of light emission.

CITATION LIST

Patent Literature

[PTL 1] JP 2003-515897 T
[PTL 2] JP 2001-313178 A
[PTL 3] JP 11-162650 A
[PTL 4] JP 11-176578 A

In order to obtain high luminous efficiency, host materials that are used with the dopant materials described above play an important role. Typical examples of the host materials proposed include 4,4'-bis(9-carbazolyl)biphenyl (hereinafter, referred to as CBP) as a carbazole compound disclosed in Patent Literature 2. When CBP is used as a host material for a green phosphorescent light-emitting material typified by a tris(2-phenylpyridine)iridium complex (hereinafter, referred to as Ir(ppy)3), the injection balance between charges is disturbed because CBP has the characteristic of facilitating the delivery of holes and not facilitating the delivery of electrons. Thus, excessively delivered holes flow out into an electron-transporting layer side, with the result that the luminous efficiency from Ir(ppy)3 lowers.

In order to provide high luminous efficiency to an organic EL device as described above, it is necessary to use a host material which has high triplet excitation energy and is striking a good balance in both charge (hole and electron)-injecting/transporting property. Further desired is a compound which has electrochemical stability, has high heat resistance, and has excellent amorphous stability, and hence further improvement has been demanded.

Patent Literature 3 discloses the indolocarbazole compound (A) shown below as a hole-transporting material.

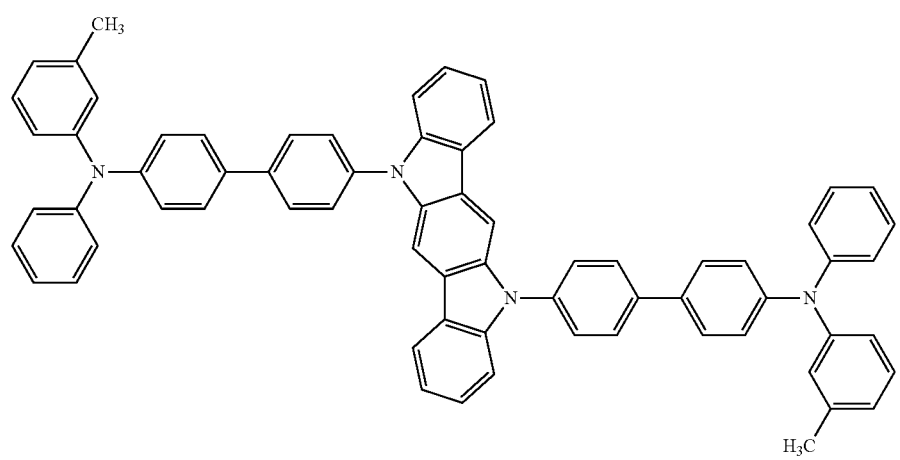

(A)

However, although the literature recommends to use, as a hole-transporting material, the compound (A) having an indolocarbazole skeleton with a specific structure and a triarylamine skeleton, the literature only discloses examples of using the compound (A) in a fluorescent light-emitting device, and does not disclose the use of the compound (A) as a material for a phosphorescent light-emitting device.

Moreover, Patent Literature 4 discloses the indolocarbazole compounds (B) and (C) shown below as hole-transporting materials.

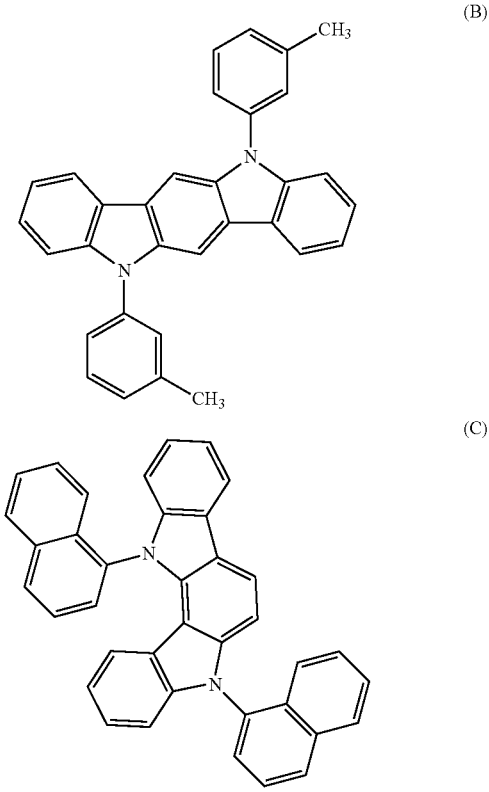

However, although the literature recommends to use these compounds having an indolocarbazole skeleton as hole-transporting materials, the literature only discloses examples of using each compound in a fluorescent light-emitting device, and does not disclose the use of the compounds as materials for a phosphorescent light-emitting device. Besides, although the literature discloses the compound (C) as an example of a charge-transporting material, the literature does not disclose specific examples thereof, and does not teach that a compound having an indolo[3,2-a]carbazole skeleton formed by substitution of a substituent of a heterocyclic ring is useful as a material for a phosphorescent light-emitting device.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device which has high luminous efficiency, has high driving stability, and is practically useful and a compound suitable for the organic EL device.

The inventors of the present invention have made intensive studies and have consequently found that, when a compound having an indolocarbazole skeleton with a specific structure is used in an organic EL device, the organic EL device exhibits excellent characteristics. As a result, the present invention has been completed.

The present invention relates to a material for a phosphorescent light-emitting device, including an indolocarbazole compound represented by the following general formula (1).

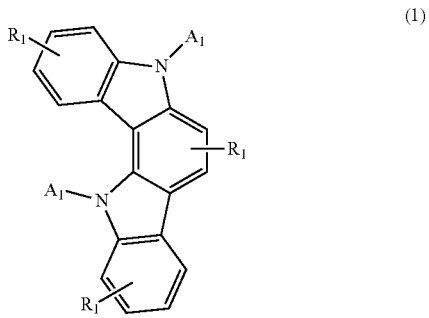

In the formula (1): $A_1$'s each independently represent an aromatic hydrocarbon group having 6 to 50 carbon atoms, an aromatic heterocyclic group having 3 to 50 carbon atoms, an alkyl group having 1 to 10 carbon atoms, or a cycloalkyl group having 3 to 11 carbon atoms, provided that at least one of $A_1$'s represents an aromatic heterocyclic group represented by the following formula (1a) or the following formula (1b) and has a fused ring structure; and $R_1$'s each independently represent a hydrogen atom, an alkyl group having 1 to 10 carbon atoms, an alkoxy group having 1 to 6 carbon atoms, or an acyl group having 2 to 6 carbon atoms.

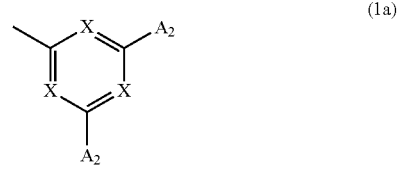

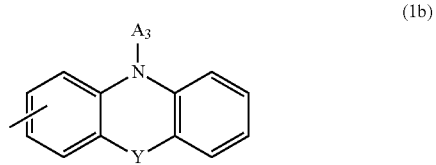

In the formula (1a), X's each independently represent a methine group or a nitrogen atom, and at least one of X's in a ring including three X's represents a nitrogen atom. In the formula (1b), Y represents a direct bond, —$NA_4$-, —O—, or —S—. In the formulae (1a) and (1b), $A_2$'s, $A_3$, and $A_4$ each independently represent an aromatic hydrocarbon group having 6 to 38 carbon atoms, an aromatic heterocyclic group having 3 to 37 carbon atoms, an alkyl group having 1 to 10 carbon atoms, or a cycloalkyl group having 3 to 11 carbon atoms.

An indolocarbazole compound in which at least one of $A_1$'s in the general formula (1) is represented by the formula (1a) is preferred. Further, it is preferred that one or both of $A_1$'s represent an aromatic heterocyclic group represented by the formula (1b) and represent no aromatic heterocyclic group represented by the formula (1a).

Further, the present invention relates to an organic electroluminescent device, including an anode, a plurality of organic layers, and a cathode laminated on a substrate, in which the organic electroluminescent device includes an organic layer containing the above-mentioned material for a phosphorescent light-emitting device.

The present invention relates, in another aspect, to a material for a phosphorescent light-emitting device, including an indolocarbazole derivative represented by the following general formula (11) or the following general formula (12).

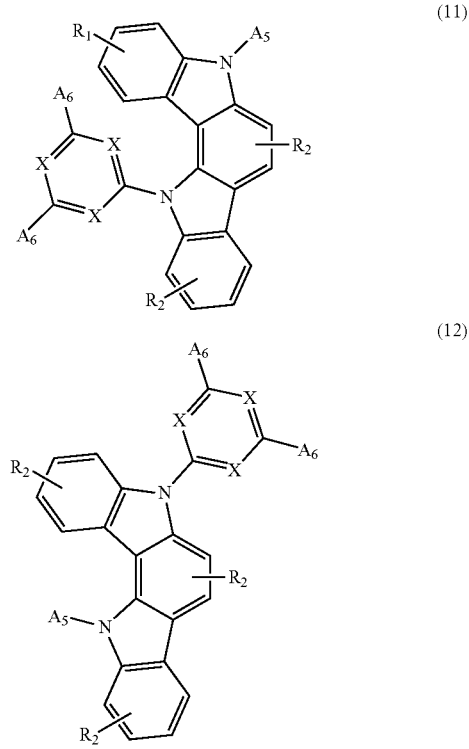

In each of the general formulae (11) and (12), X's each independently represent a methine group or a nitrogen atom, and at least one of X's in a ring including three X's represents a nitrogen atom. $A_5$ represents an aromatic hydrocarbon group having 6 to 38 carbon atoms, an aromatic heterocyclic group having 3 to 37 carbon atoms, an alkyl group having 1 to 10 carbon atoms, or a cycloalkyl group having 3 to 11 carbon atoms, and $A_6$'s each represent an aromatic hydrocarbon group having 6 to 18 carbon atoms, an aromatic heterocyclic group having 3 to 17 carbon atoms, an alkyl group having 1 to 10 carbon atoms, or a cycloalkyl group having 3 to 11 carbon atoms. At least one of $A_5$ and $A_6$'s represents an aromatic hydrocarbon group having 10 to 18 carbon atoms or an aromatic heterocyclic group having 6 to 17 carbon atoms, each formed of two or more rings. $R_2$'s each independently represent a hydrogen atom, an alkyl group having 1 to 10 carbon atoms, an alkoxy group having 1 to 6 carbon atoms, or an acyl group having 2 to 6 carbon atoms.

A material for a phosphorescent light-emitting device including an indolocarbazole derivative represented by the general formula (11) or (12) is contained in an organic layer in an organic electroluminescent device as a material for a phosphorescent light-emitting device including an indolocarbazole derivative represented by the general formula (1) is. The material for a phosphorescent light-emitting device including an indolocarbazole derivative represented by the general formula (11) or (12) is advantageously contained in at least one layer selected from the group consisting of a light-emitting layer, a hole-transporting layer, an electron-transporting layer, and a hole-blocking layer, and is more advantageously contained in a light-emitting layer or a hole-transporting layer containing a phosphorescent light-emitting dopant.

DESCRIPTION OF EMBODIMENTS

Figure 1:
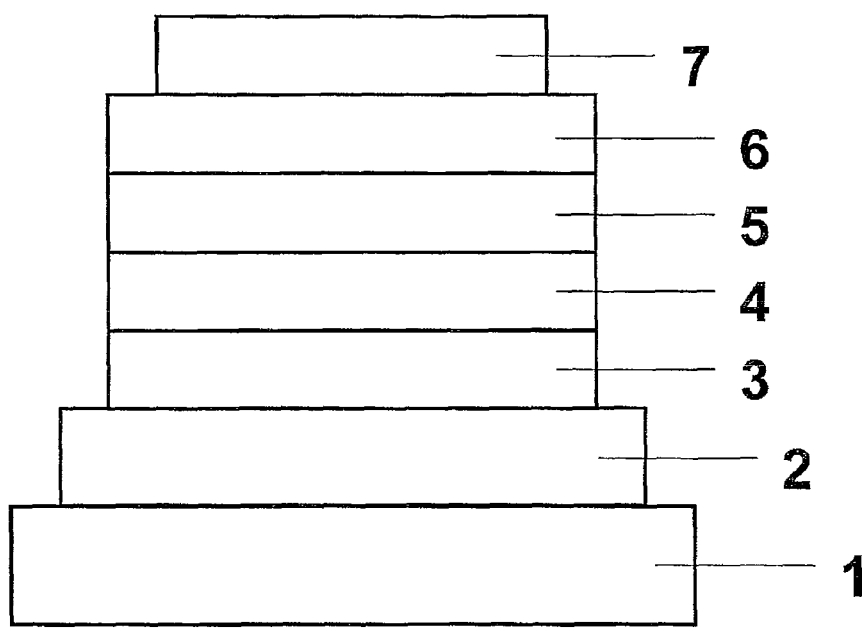
FIG. 1 is a cross-sectional view showing one structural example of an organic EL device.

A material for a phosphorescent light-emitting device of the present invention is an indolocarbazole compound represented by the general formula (1). The skeleton of this indolocarbazole compound has a structure in which a central benzene ring fused with two nitrogen-containing, five-membered rings is included, and when the position of the carbon atom in the benzene ring bonded to the nitrogen atom in one of the nitrogen-containing, five-membered rings is defined as position 1, the nitrogen atom in the other nitrogen-containing, five-membered ring bonded to the carbon atom at position 3 in the benzene ring. Thus, the indolocarbazole compound is expected to bring about the excellent effects described below.

In the general formula (1), $A_1$'s each independently represent an aromatic hydrocarbon group having 6 to 50 carbon atoms, an aromatic heterocyclic group having 3 to 50 carbon atoms, an alkyl group having 1 to 10 carbon atoms, or a cycloalkyl group having 3 to 11 carbon atoms. A1's each preferably represents an aromatic hydrocarbon group having 6 to 38 carbon atoms, an aromatic heterocyclic group having 3 to 37 carbon atoms, an alkyl group having 1 to 4 carbon atoms, a cycloalkyl group having 3 to 8 carbon atoms, or a group represented by the formula (1a) or the formula (1b).

In the general formula (1), when $A_1$'s each represent an aromatic hydrocarbon group or an aromatic heterocyclic group, specific examples of the aromatic hydrocarbon group or the aromatic heterocyclic group include a monovalent group produced by removing one hydrogen atom from benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, phenanthridine, phenanthroline, acridine, phenazine, phenoxazine, phenothiazine, anthyridine, or an aromatic compound in which a plurality of those aromatic rings are linked together. Of those, a monovalent group produced by removing one hydrogen atom from benzene, pyridine, pyrimidine, triazine, naphthalene, quinoline, isoquinoline, quinoxaline, naphthyridine, anthracene, phenanthrene, pyrene, or an aromatic compound in which a plurality of those aromatic rings are linked together is preferably given, and a monovalent group produced by removing one hydrogen atom from benzene, pyridine, pyrimidine, triazine, naphthalene, or an aromatic compound in which a plurality of those aromatic rings are linked together is more preferably given. When a plurality of the above-mentioned aromatic rings are linked together, the rings may be identical to or different from each other. Specific examples of the monovalent group produced by removing one hydrogen atom from an aromatic compound in which a plurality of the above-mentioned aromatic rings are linked together include a group produced by removing a hydrogen atom from, for example, biphenyl, terphenyl, bipyridine, bipyrimidine, bitriazine, bistriazylbenzene, binaphthalene, phenylpyridine, diphenylpyridine, diphenylpyrimidine, diphenyltriazine, phenylcarbazole, or pyridylcarbazole. The position in such monovalent group at which the group is linked to a nitrogen atom of the indolocarbazole is not particularly limited, and may be on a terminal ring or on a middle ring. Those groups may have each have a substituent, and when having a substituent, the substituent is preferably an alkyl group having 1 to 4 carbon atoms, an alkoxy group having 1 or 2 carbon atoms, or an acetyl group. When a group herein has a substituent, the count of the number of carbon atoms includes the number of carbon atoms in the substituent.

Here, the monovalent group produced by the linkage of a plurality of aromatic rings is, for example, represented by the following formulae.

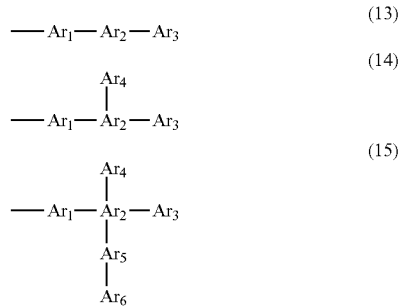

(In the formulae (11) to (13), $Ar_1$ to $Ar_6$ each represent a substituted or unsubstituted aromatic ring.)

When any one of $A_1$ to $A_4$ herein represents an aromatic compound in which a plurality of aromatic rings are linked together, the aromatic hydrocarbon group refers to the case where $Ar_1$ in the formulae (13) to (15) represents an aromatic hydrocarbon, and the aromatic heterocyclic group refers to the case where $Ar_1$ represents an aromatic heterocyclic ring.

In the general formula (1), when $A_1$'s each represent an alkyl group having 1 to 10 carbon atoms, specific examples thereof include a methyl group, an ethyl group, a propyl group, a butyl group, a pentyl group, a hexyl group, a heptyl group, an octyl group, a nonyl group, and a decyl group. The above-mentioned alkyl group may be linear or branched.

In the general formula (1), when $A_1$'s each represent a cycloalkyl group having 3 to 11 carbon atoms, specific examples thereof include a cyclopropyl group, a cyclobutyl group, a cyclopentyl group, a cyclohexyl group, a cycloheptyl group, a cyclooctyl group, and a methylcyclohexyl group. Of those, a cyclohexyl group and a methylcyclohexyl group are preferably given.

In the formula (1a), X's each independently represent a methine group or a nitrogen atom, and at least one X in the ring including X's represents a nitrogen atom.

In the formula (1b), Y represents a direct bond, —$NA_5$-, —O—, or —S—, preferably a direct bond.

In the formulae (1a) and (1b), $A_2$'s, $A_3$, and $A_4$ each independently represent an aromatic hydrocarbon group having 6 to 38 carbon atoms, an aromatic heterocyclic group having 3 to 37 carbon atoms, an alkyl group having 1 to 10 carbon atoms, or a cycloalkyl group having 3 to 11 carbon atoms.

$A_2$'s, $A_3$, and $A_4$ each preferably represent an aromatic hydrocarbon group having 6 to 18 carbon atoms, an aromatic heterocyclic group having 3 to 17 carbon atoms, an alkyl group having 1 to 4 carbon atoms, or a cycloalkyl group having 3 to 8 carbon atoms.

When any one of $A_2$'s, $A_3$, and $A_4$ represents an aromatic hydrocarbon group or an aromatic heterocyclic group, specific examples thereof include a monovalent group produced by removing one hydrogen atom from benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, phenoxazine, phenothiazine, or an aromatic compound in which a plurality of those aromatic rings are linked together. Of those, a monovalent group produced by removing one hydrogen atom from benzene, pyridine, pyrimidine, triazine, naphthalene, quinoline, isoquinoline, quinoxaline, naphthyridine, anthracene, phenanthrene, pyrene, or an aromatic compound in which a plurality of those aromatic rings are linked together is preferably given, and a monovalent group produced by removing one hydrogen atom from benzene, pyridine, pyrimidine, triazine, naphthalene, an aromatic compound in which a plurality of those aromatic rings are linked together is more preferably given. When a plurality of the above-mentioned aromatic rings are linked together, the rings may be identical to or different from each other. Specific examples of the monovalent group produced by removing one hydrogen atom from an aromatic compound in which a plurality of the above-mentioned aromatic rings are linked together include a group produced by removing a hydrogen atom from, for example, biphenyl, terphenyl, bipyridine, bipyrimidine, bitriazine, bistriazylbenzene, binaphthalene, phenylpyridine, diphenylpyridine, diphenylpyrimidine, diphenyltriazine, phenylcarbazole, or pyridylcarbazole. The position in such monovalent group at which the group is linked to a nitrogen atom of the indolocarbazole is not particularly limited, and may be on a terminal ring or on a middle ring. Those groups may each have a substituent. When any one of the groups has a substituent, the substituent is preferably an alkyl group having 1 to 4 carbon atoms, an alkoxy group having 1 or 2 carbon atoms, or an acetyl group.

When any one of $A_2$'s, $A_3$, and $A_4$ represents an alkyl group or a cycloalkyl group in the formulae (1a) and (1b), specific examples thereof and the preferred range thereof are the same as those for $A_1$'s.

Two $A_1$'s are present in the general formula (1), and one or both of $A_1$'s must each represent an aromatic heterocyclic group represented by the formula (1a) or (1b). Moreover, at least one $A_1$ must have a fused ring structure. This fused ring structure may be directly bonded to a nitrogen atom in the indolocarbazole ring, or may exist by being bonded to a group which is bonded to a nitrogen atom and does not have a fused ring structure. For example, an aromatic heterocyclic group represented by the formula (1b) has a fused ring structure, and hence the above-mentioned requirements are satisfied when the general formula (1) has one or more aromatic heterocyclic groups of this kind. An aromatic heterocyclic group represented by the formula (1a) satisfies the above-mentioned requirements if one of the substituents $A_2$ has a fused ring structure, but when the substituents $A_2$ have no fused ring structure, the other $A_1$ must represent a group having a fused ring structure. An aromatic hydrocarbon group or an aromatic heterocyclic group each formed of two or more rings is preferred as the fused ring structure, and an aromatic heterocyclic group represented by the formula (1b) is preferred as an aromatic heterocyclic group having a fused ring structure.

Specifically, at least one of $A_1$'s and $A_2$'s has a fused ring structure formed of two or more rings in the general formula (1) and the formula (1a). Here, when a plurality of aromatic rings are link together, the fused ring structure refers to the case where $Ar_1$ in the formulae (13) to (15) is formed of two or more rings. That is, for $A_1$'s, the fused ring structure refers to the case where a ring directly bonded to a nitrogen atom on the indolocarbazole is formed of two or more rings, and for $A_2$, refers to the case where a ring directly bonded to the aromatic heterocyclic ring is formed of two or more rings. Note that, as described above, a plurality of aromatic rings including those having no fused ring structure may be link together in each of $A_1$'s and $A_2$'s. Preferred specific examples of the aromatic hydrocarbon group or aromatic heterocyclic group having a fused ring structure include a monovalent group produced by removing one hydrogen atom from naphthalene, quinoline, isoquinoline, quinoxaline, naphthyridine, anthracene, phenanthrene, pyrene, carbazole, phenanthridine, phenanthroline, acridine, phenazine, phenoxazine, phenothiazine, or anthyridine. Of those, a monovalent group produced by removing one hydrogen atom from naphthalene, quinoline, isoquinoline, pyrene, carbazole, acridine, phenazine, phenoxazine, or phenothiazine is preferably given. Preferred specific examples of the aromatic hydrocarbon group or aromatic heterocyclic group having a fused ring structure include a monovalent group produced by removing one hydrogen atom from naphthalene, quinoline, isoquinoline, quinoxaline, naphthyridine, anthracene, phenanthrene, pyrene, carbazole, phenanthridine, phenanthroline, acridine, phenazine, phenoxazine, phenothiazine, or anthyridine. Of those, a monovalent group produced by removing one hydrogen atom from naphthalene, quinoline, isoquinoline, pyrene, carbazole, acridine, phenazine, phenoxazine, or phenothiazine is preferably given.

In the general formula (1), a plurality of $R_1$'s each independently represent a hydrogen atom, an alkyl group having 1 to 10 carbon atoms, an alkoxy group having 1 to 6 carbon atoms, or an acyl group having 2 to 6 carbon atoms, preferably a hydrogen atom, an alkyl group having 1 to 4 carbon atoms, an alkoxy group having 1 or 2 carbon atoms, or an acyl group having 2 carbon atoms, more preferably a hydrogen atom.

It is also preferred that the material for a phosphorescent light-emitting device of the present invention be an indolocarbazole compound represented by the general formula (11) or (12).

In the general formulae (11) and (12), X's each independently represent a methine group or a nitrogen atom, and in the ring including three X's, at least one X represents a nitrogen atom. $A_5$ represents an aromatic hydrocarbon group having 6 to 38 carbon atoms, an aromatic heterocyclic group having 3 to 37 carbon atoms, an alkyl group having 1 to 10 carbon atoms, or a cycloalkyl group having 3 to 11 carbon atoms, and $A_6$'s each independently represent an aromatic hydrocarbon group having 6 to 18 carbon atoms, an aromatic heterocyclic group having 3 to 17 carbon atoms, an alkyl group having 1 to 10 carbon atoms, or a cycloalkyl group having 3 to 11 carbon atoms, provided that at least one of $A_6$'s in each general formula represents an aromatic hydrocarbon group having 6 to 18 carbon atoms or an aromatic heterocyclic group having 3 to 17 carbon atoms. $R_2$'s each independently represent a hydrogen atom, an alkyl group having 1 to 10 carbon atoms, an alkoxy group having 1 to 6 carbon atoms, or an acyl group having 2 to 6 carbon atoms.

When any one of $A_5$, $A_6$'s, and $R_2$'s represents an aromatic hydrocarbon group, an aromatic heterocyclic group, an alkyl group, a cycloalkyl group, or an acyl group in the general formulae (11) and (12), the descriptions about those groups are common to those given in the general formula (1). However, when the number of carbon atoms is limited in the general formulae (11) and (12), the number of carbon atoms is not out of the range of the limited number. Further, at least one of $A_5$ and $A_6$'s in each general formula preferably has a fused ring structure formed of two or more rings.

An indolocarbazole compound represented by the general formula (1) can be synthesized by selecting materials depending on the structure of a target compound and using a known technique.

One method of synthesizing the above-mentioned indolocarbazole compound includes causing a hydrogen chloride gas to act on indole to synthesize its dimer by using palladium carbon, causing the dimer to react with N,N-dimethylacetaldehyde diethyl acetal in an acetic acid solvent to synthesize indolo[3,2-a]carbazole, and introducing any of various kinds of substituents to indolo[3,2-a]carbazole by using a coupling reaction.

Specific examples of the indolocarbazole compound represented by the general formula (1) are shown below, but the indolocarbazole compound is not limited to these examples.

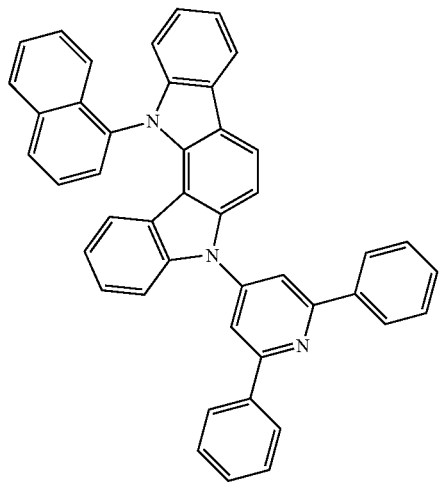

1

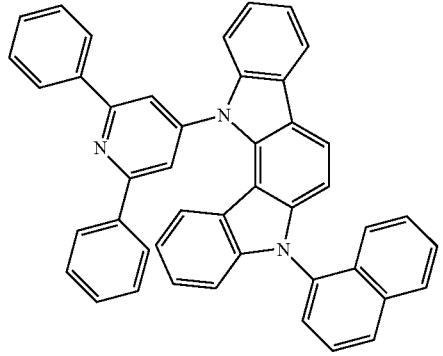

2

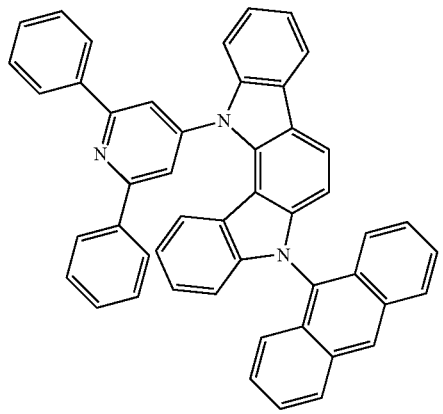

3

-continued
4
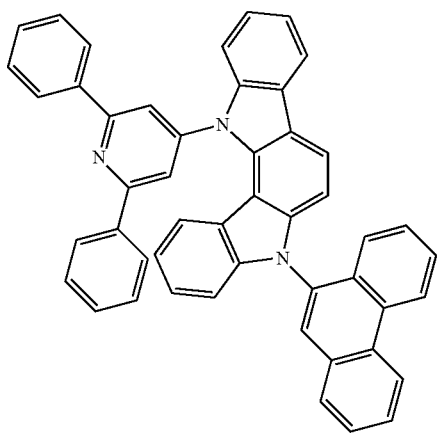
5
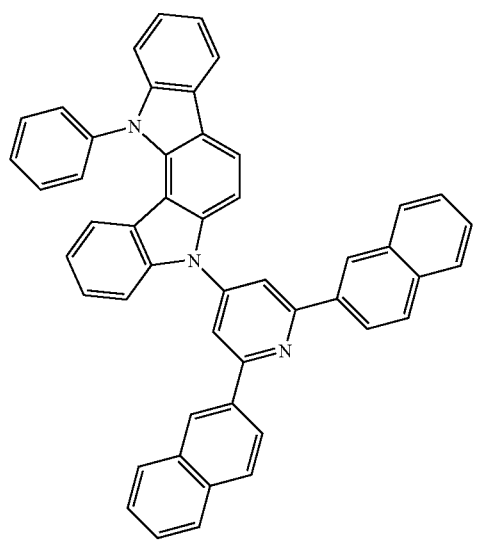
6
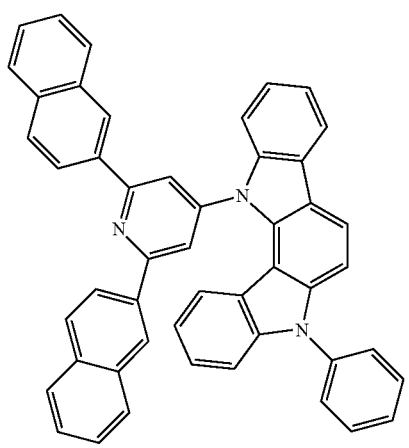
-continued
7
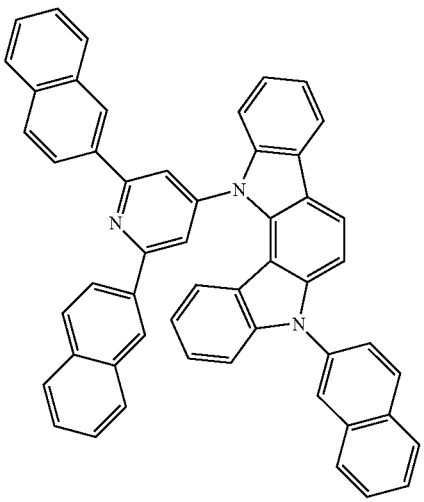
8
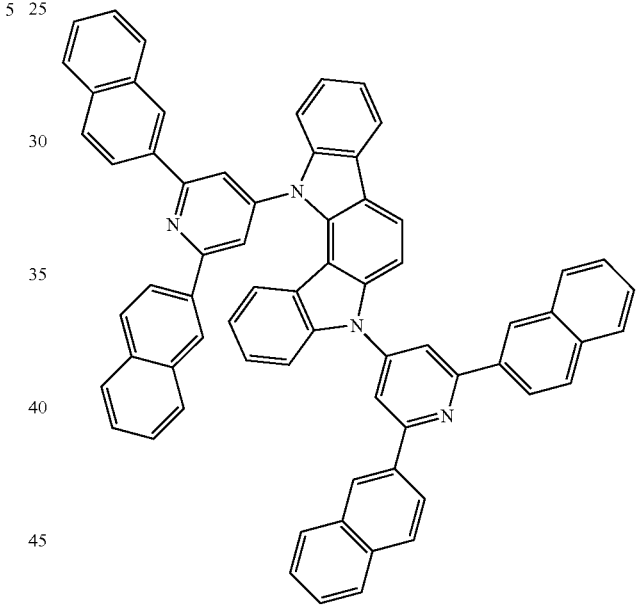
9
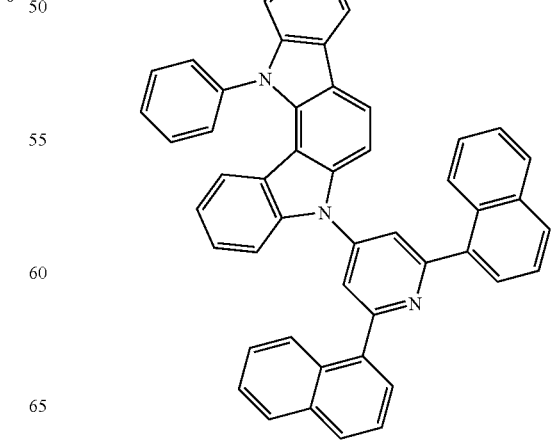

10
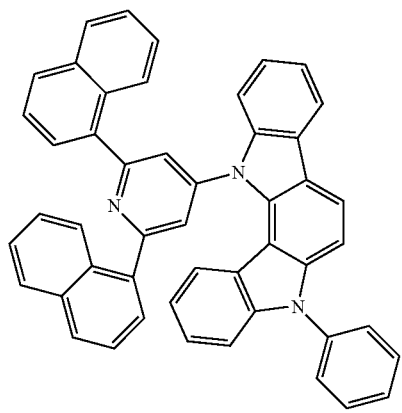
11
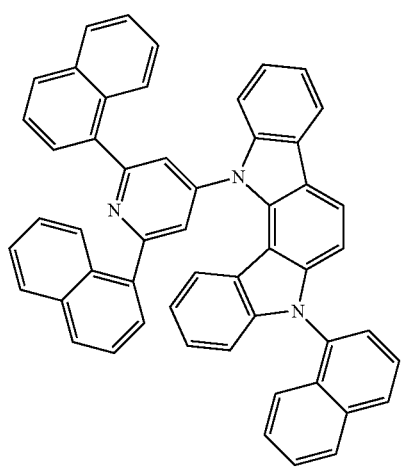
12
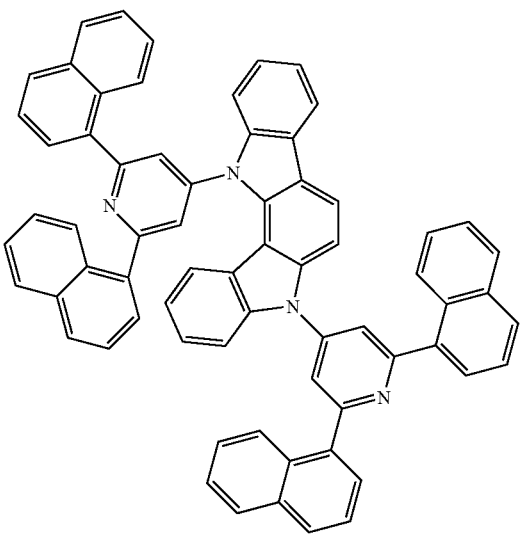
13
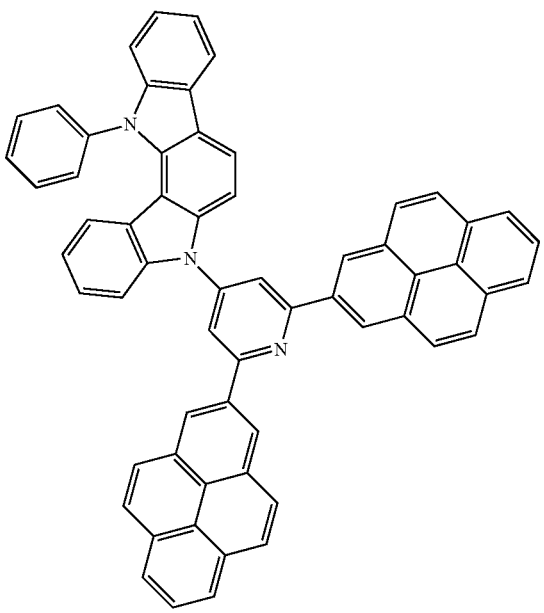
14
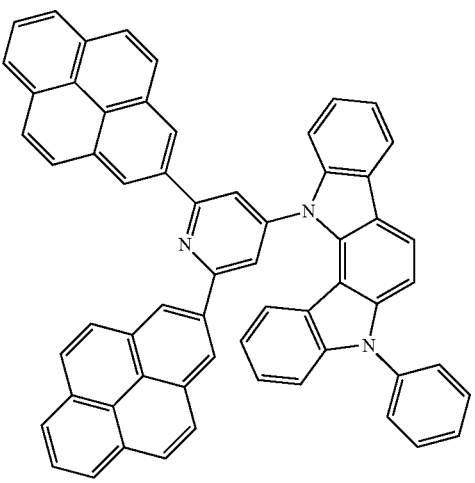
15
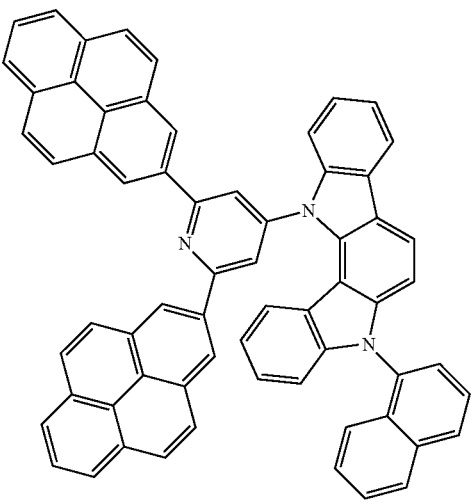

16
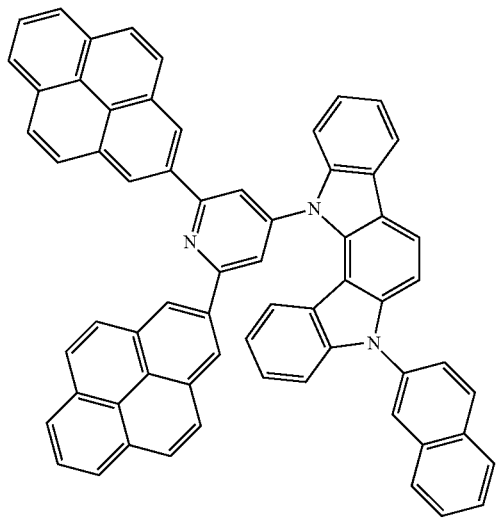
17
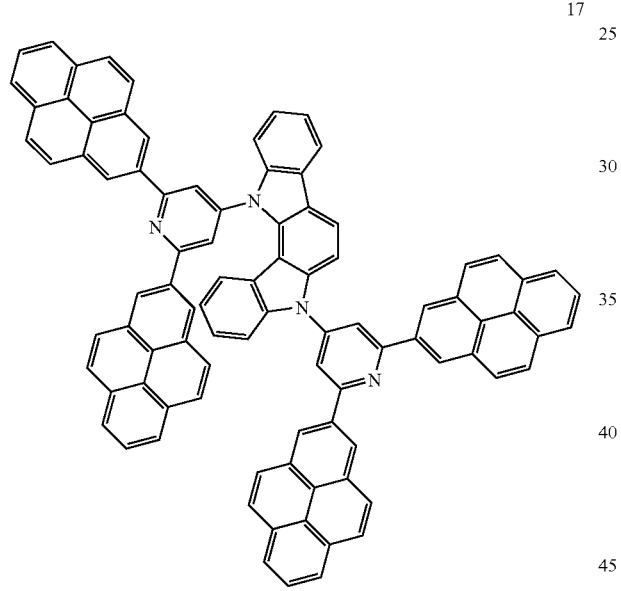
18
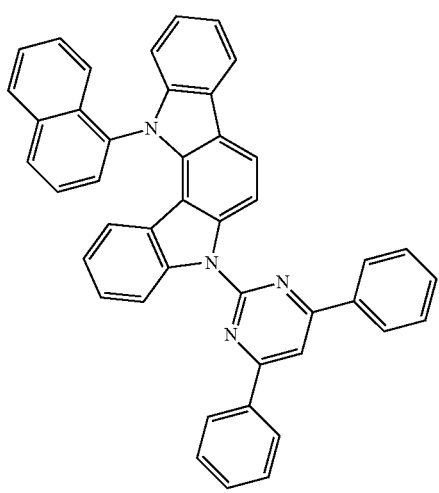
19
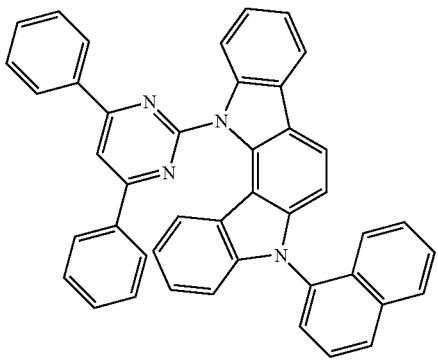
20
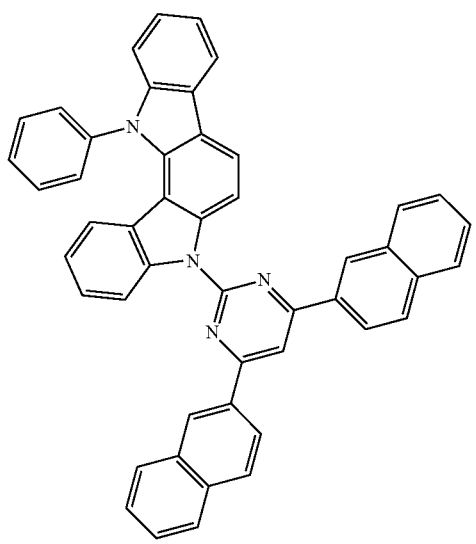
21
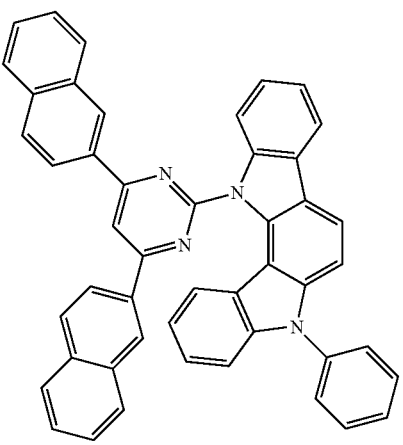

-continued
22
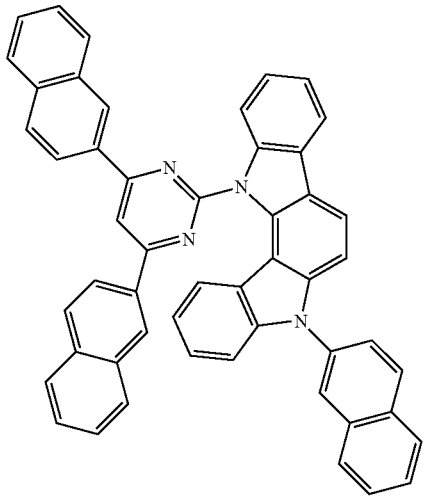
23
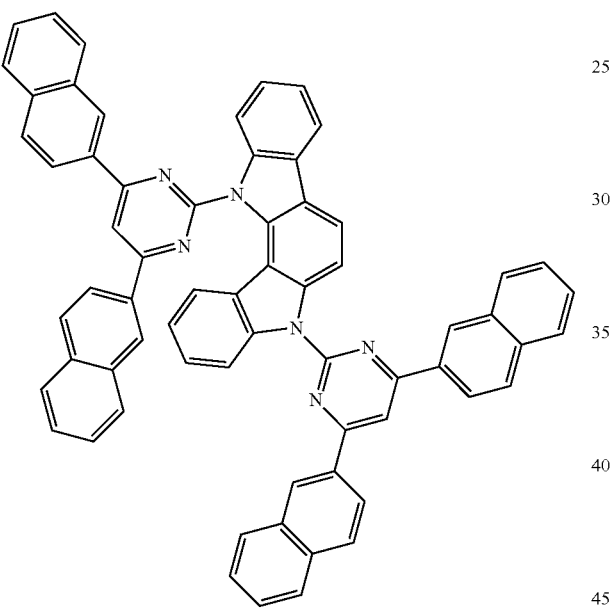
24
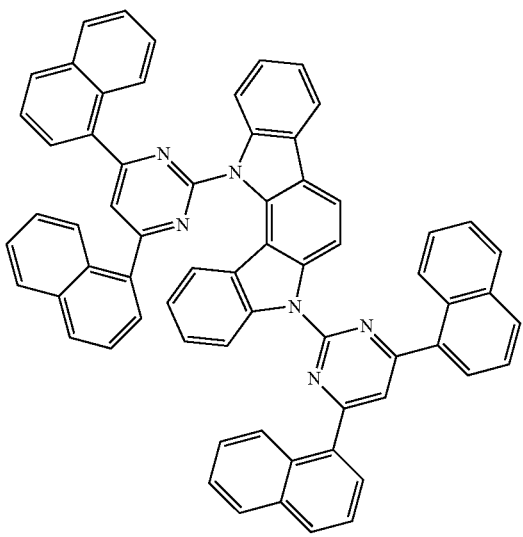
-continued
25
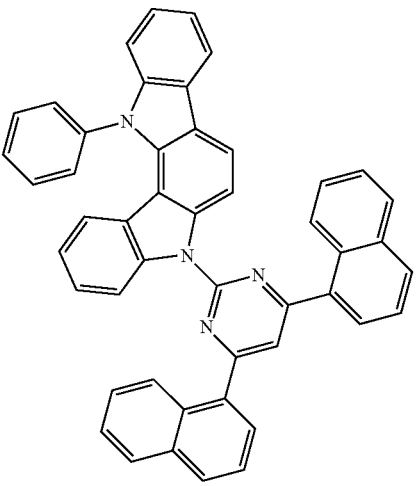
26
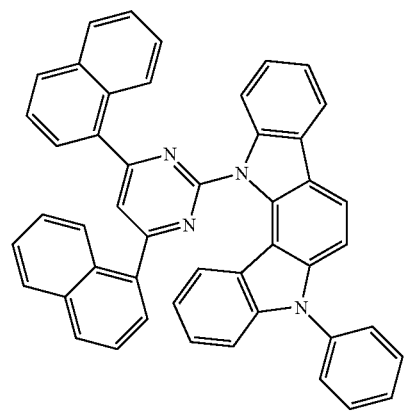
27
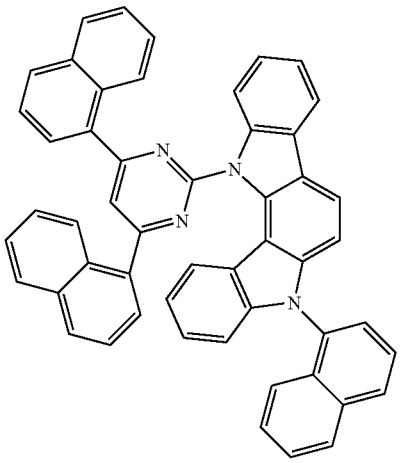

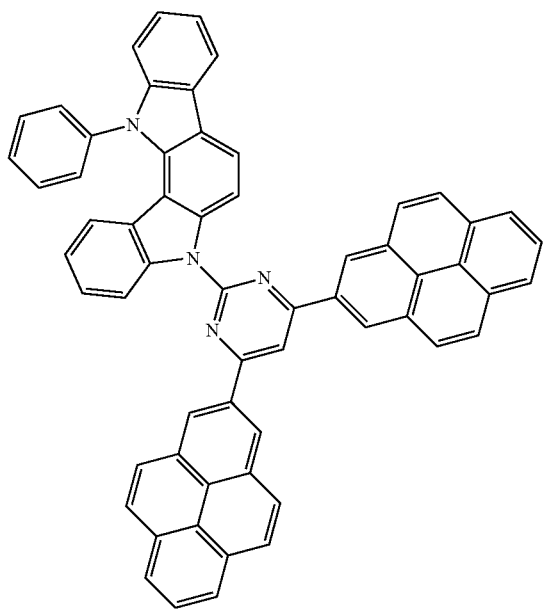
28
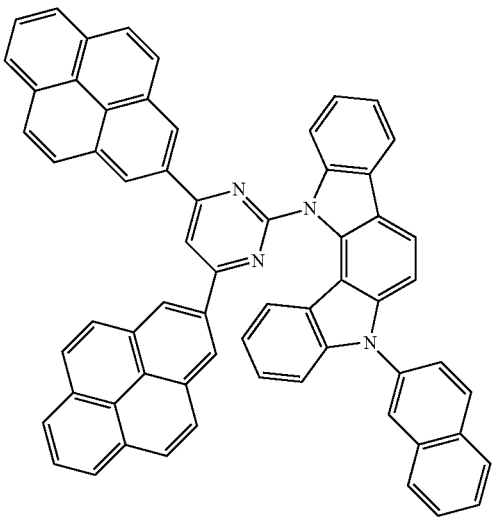
31
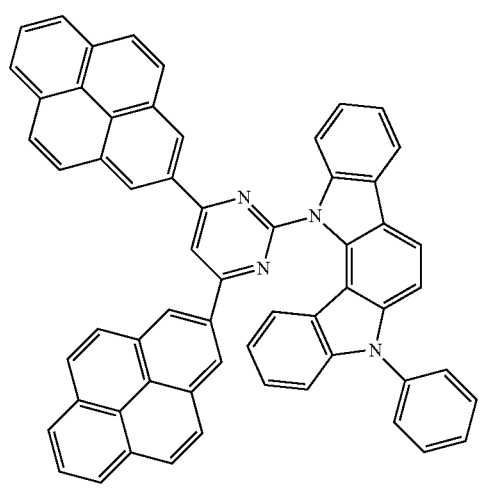
29
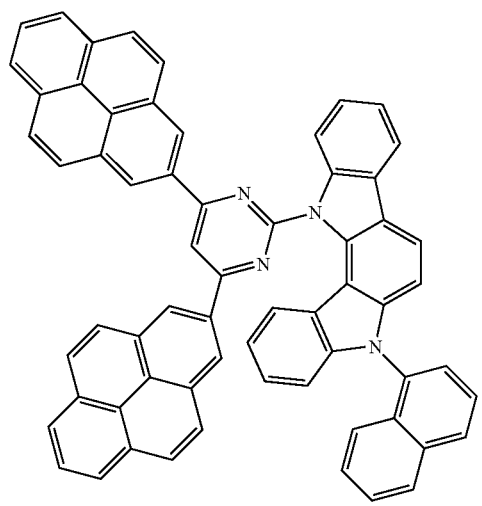
30
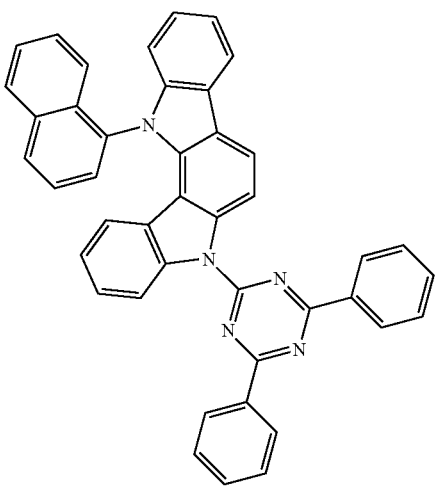
32
33

34
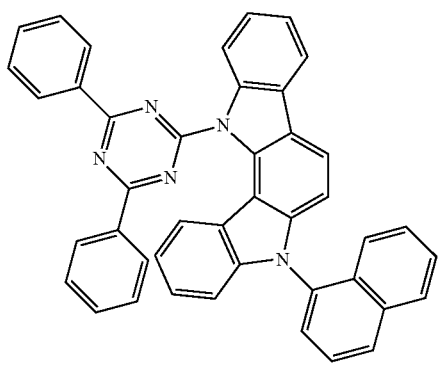
35
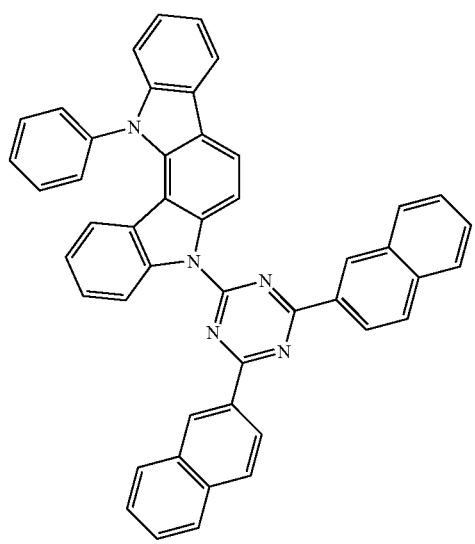
36
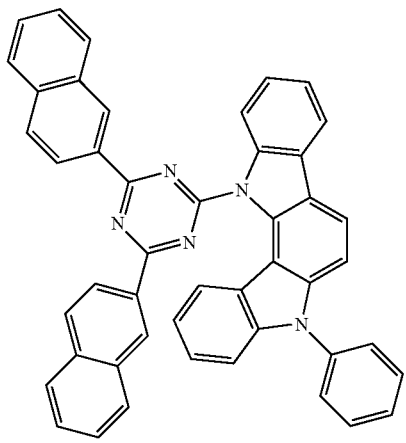
37
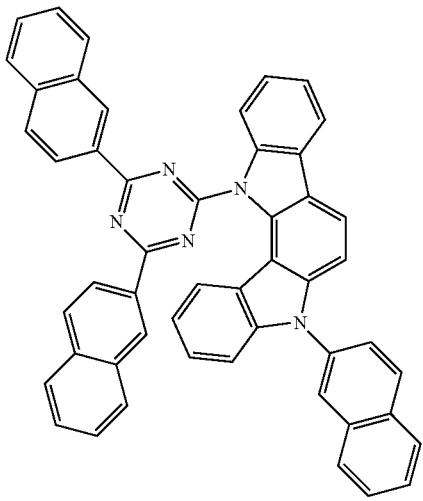
38
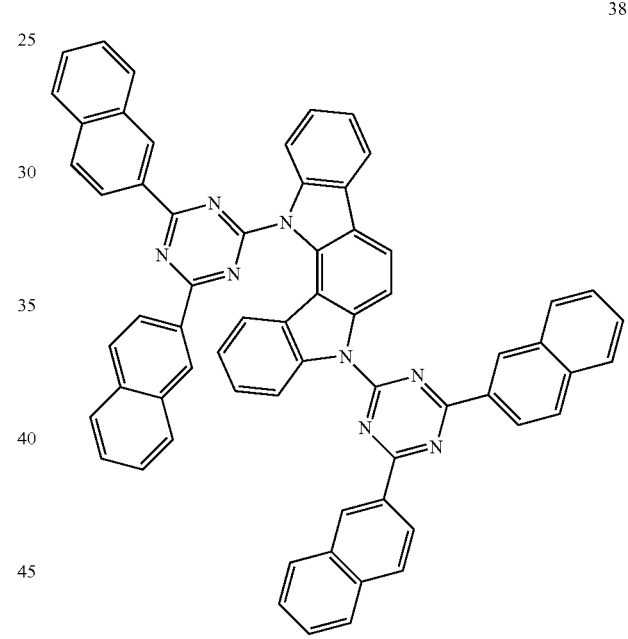
39
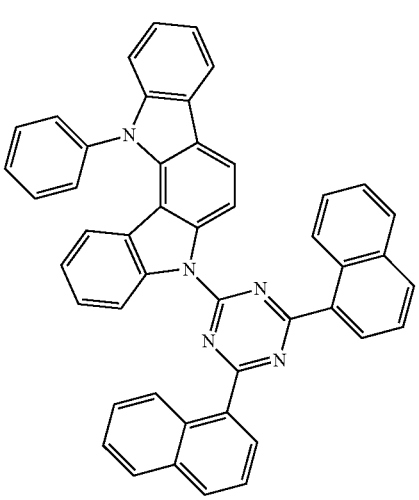

40
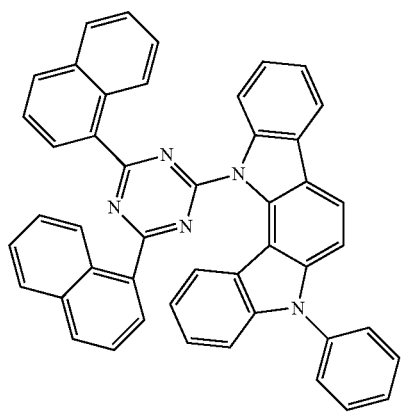
41
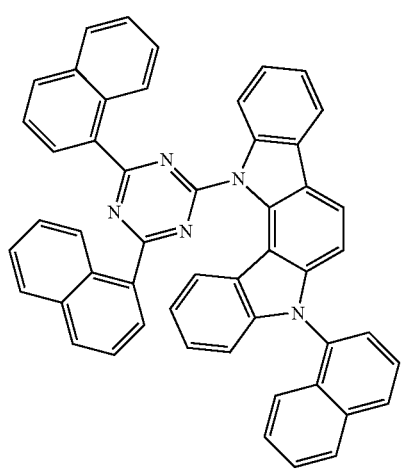
42
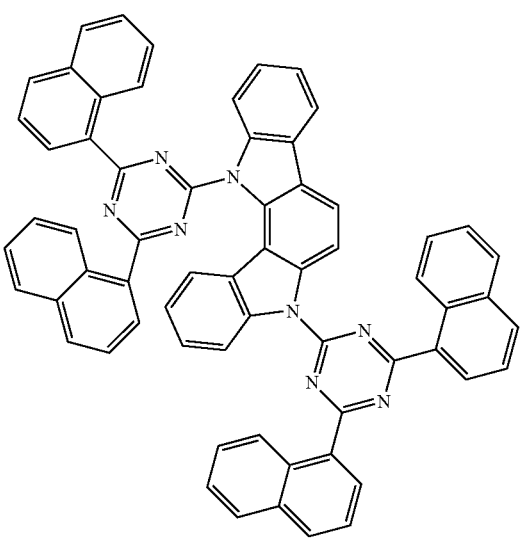
43
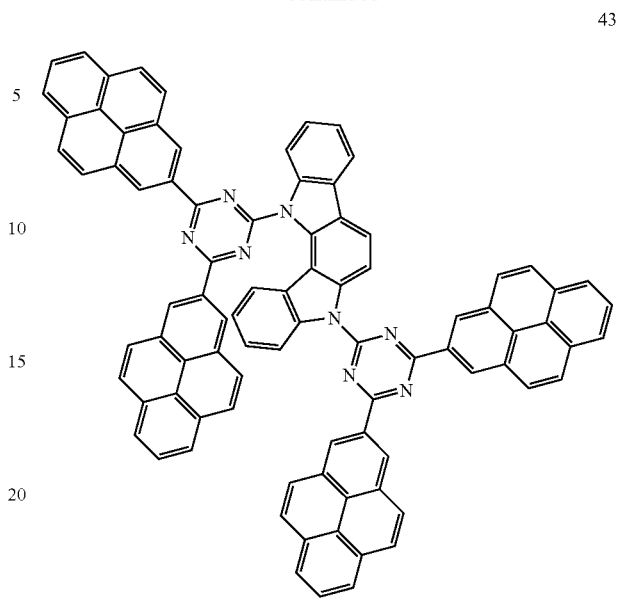
44
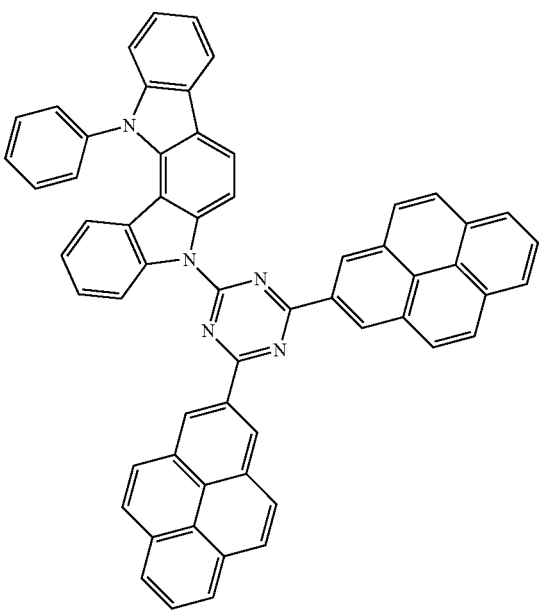

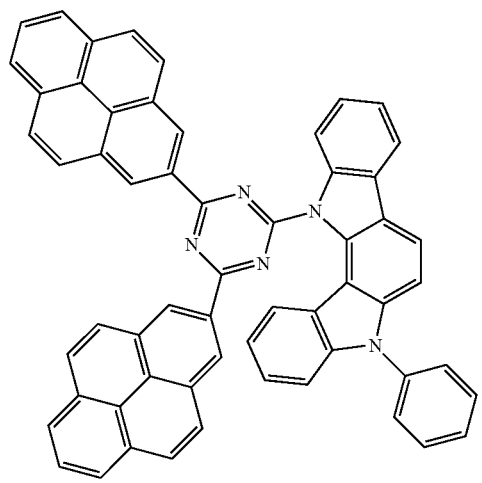
45
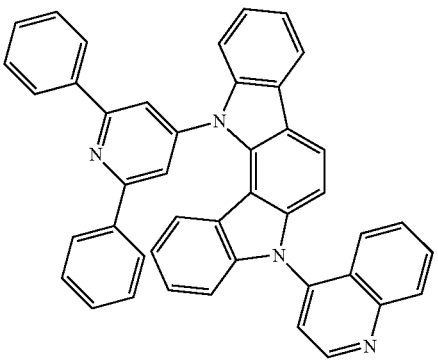
48
46
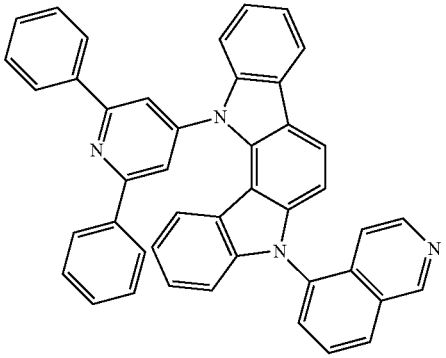
49
47
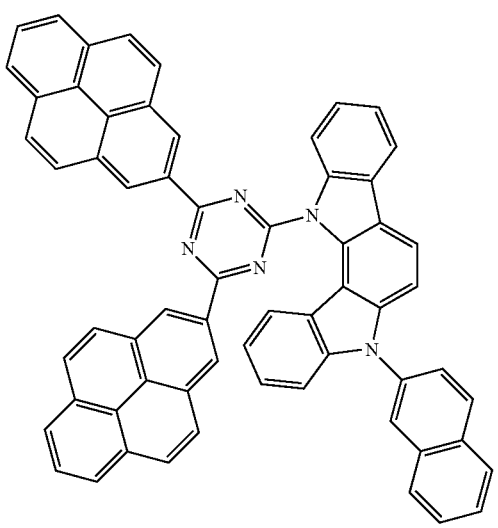
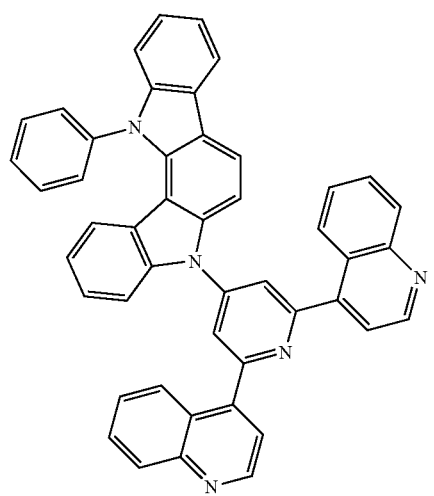
50

51
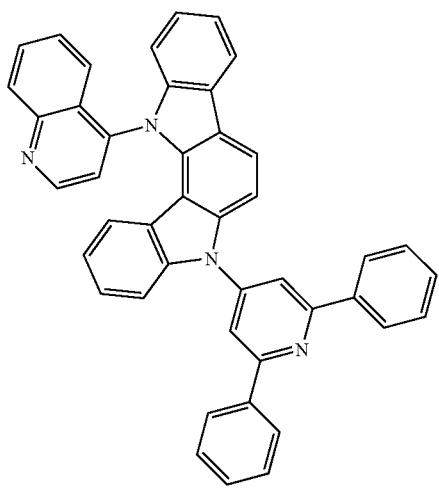
52
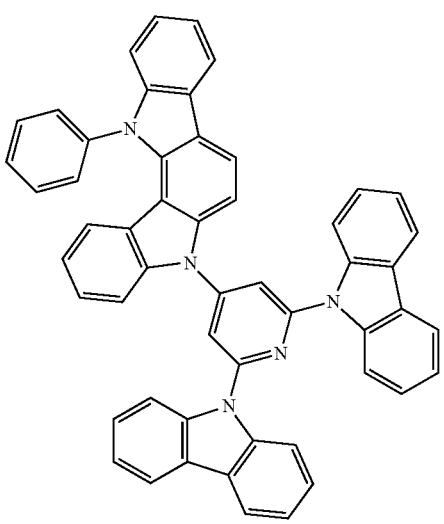
53
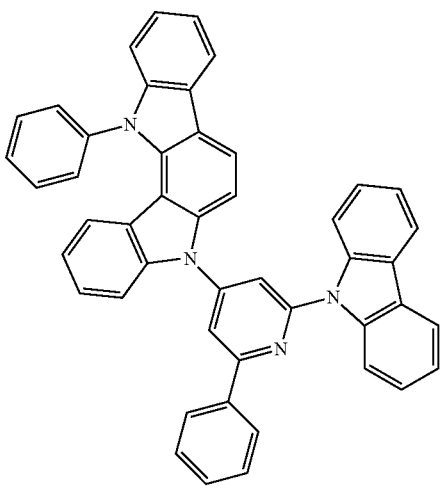
54
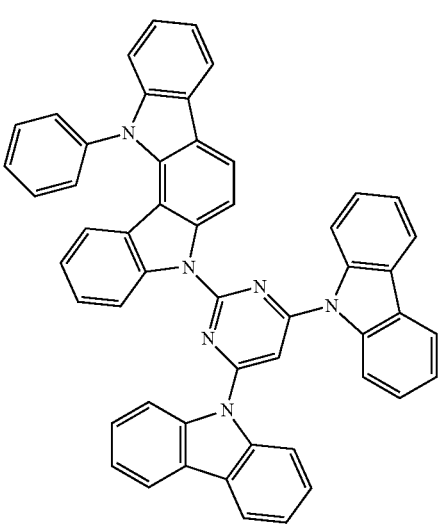
55
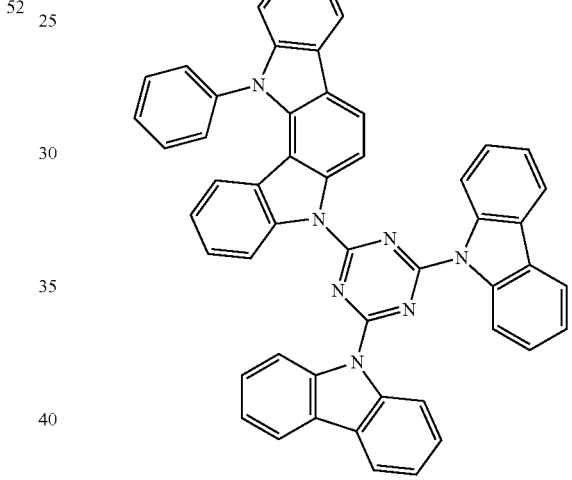
56
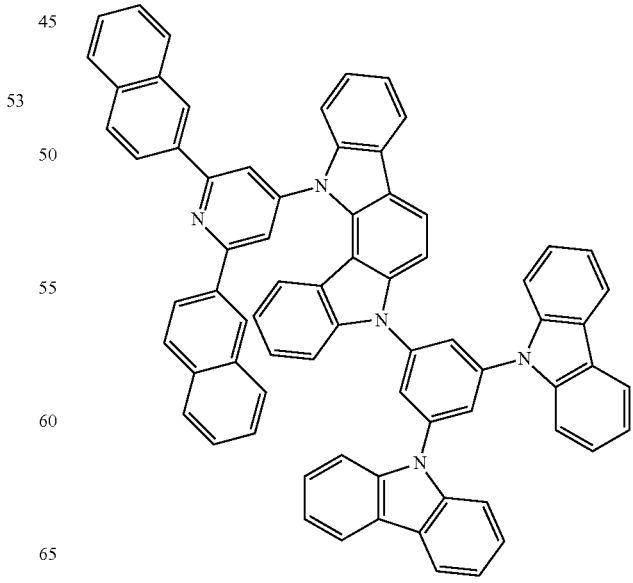

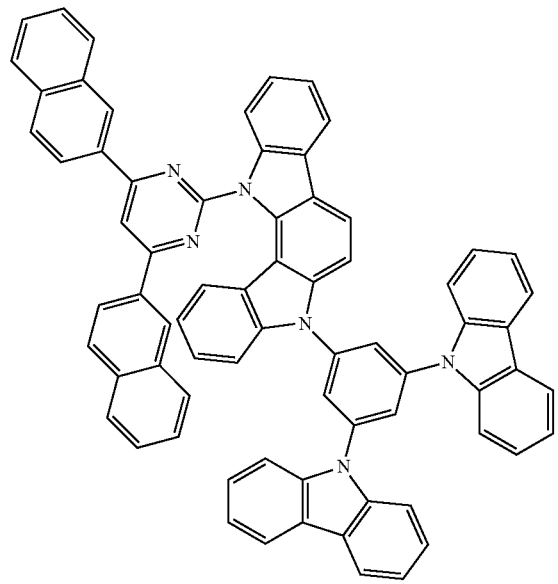
57
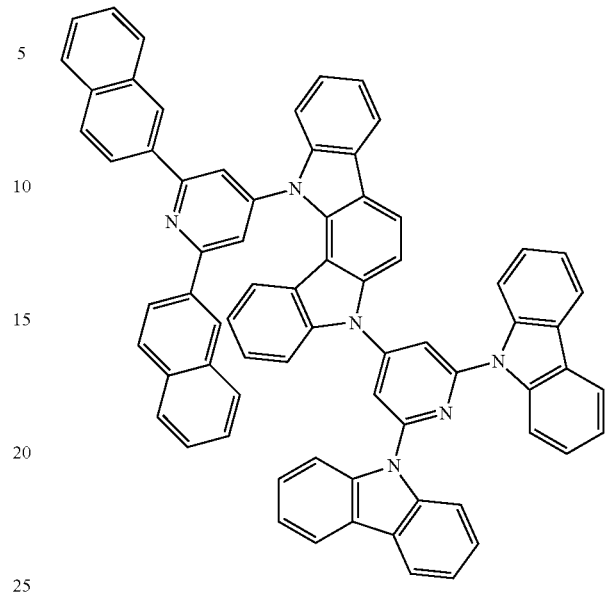
59
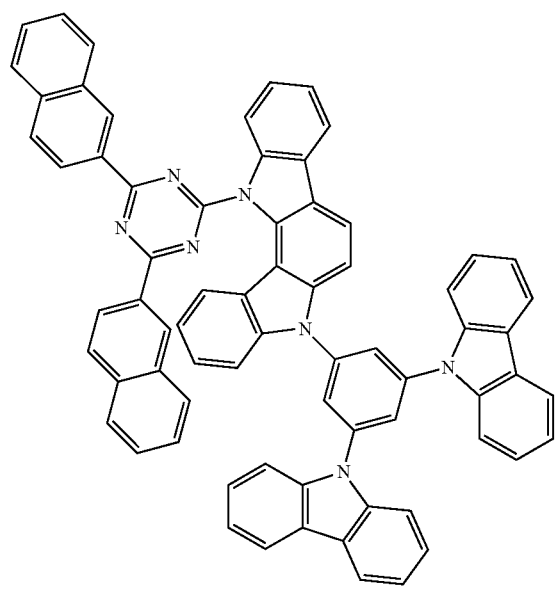
58
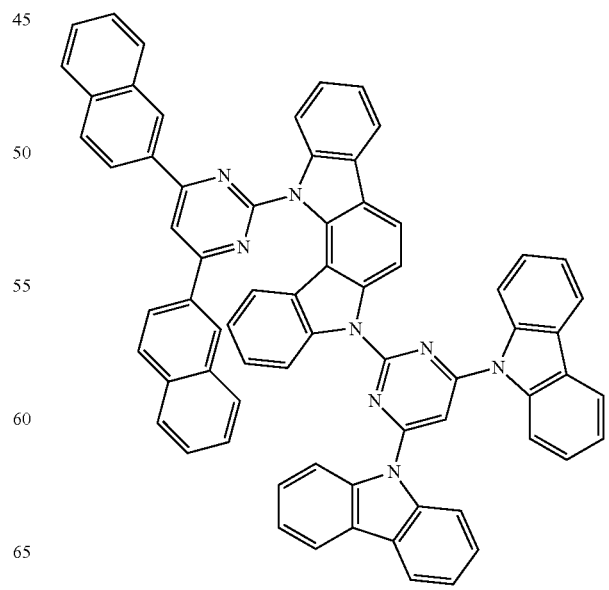
60

61
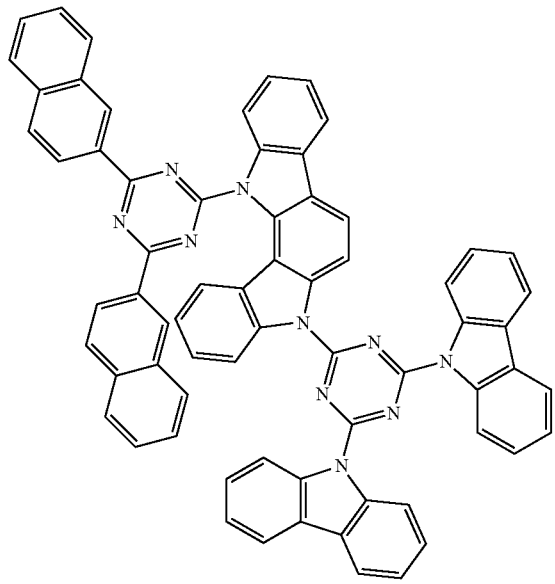
62
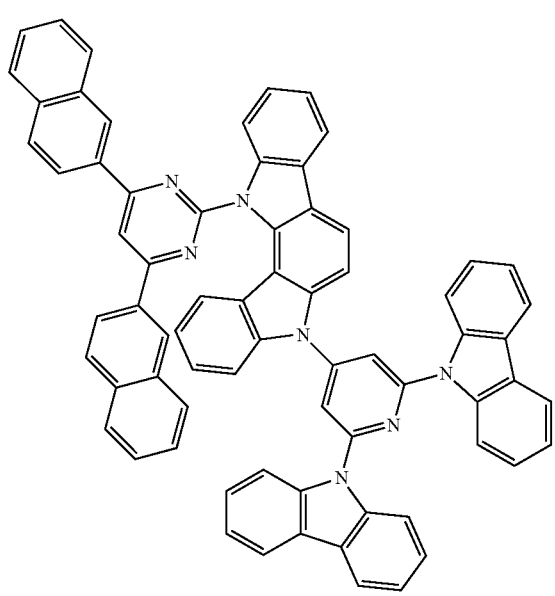
63
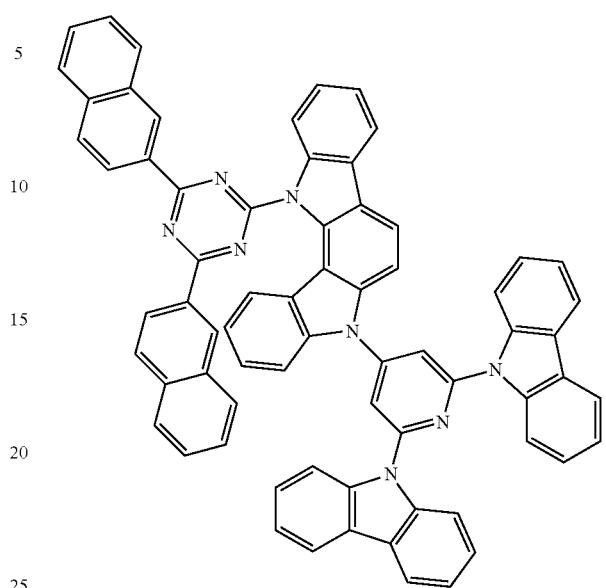
64
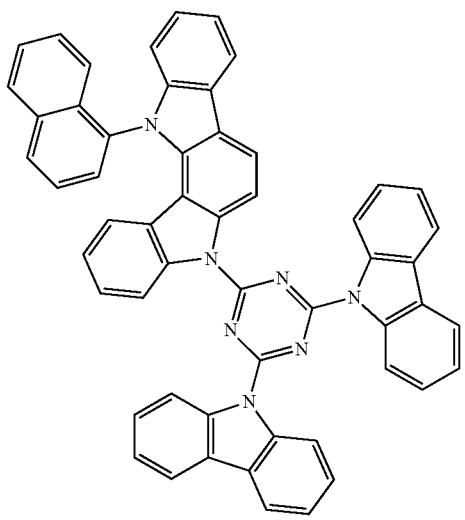
65
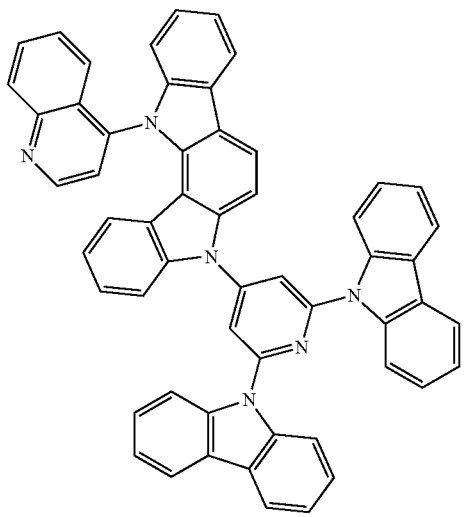

66
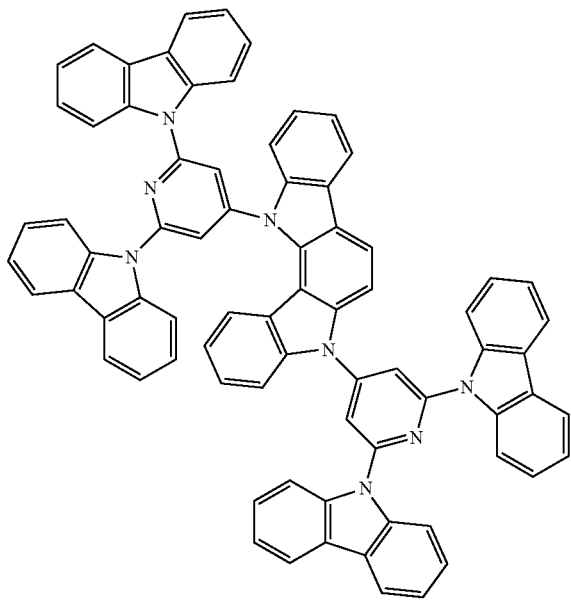
68
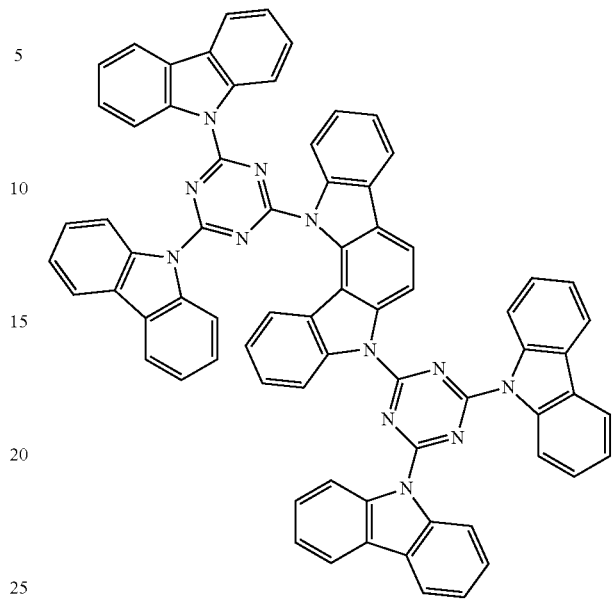
67
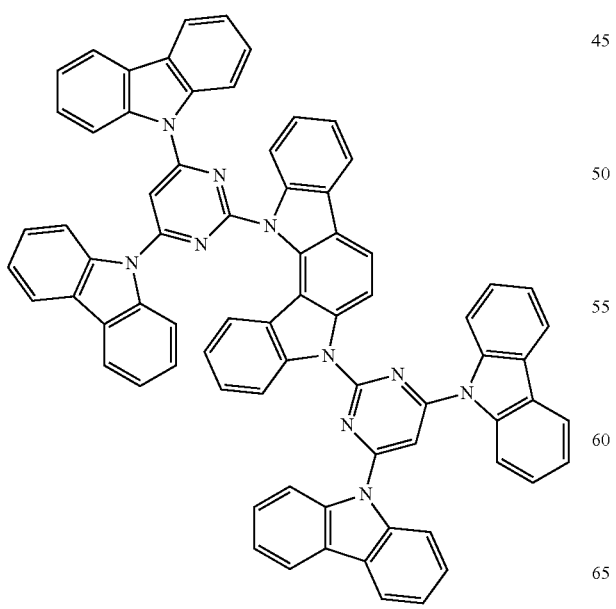
69
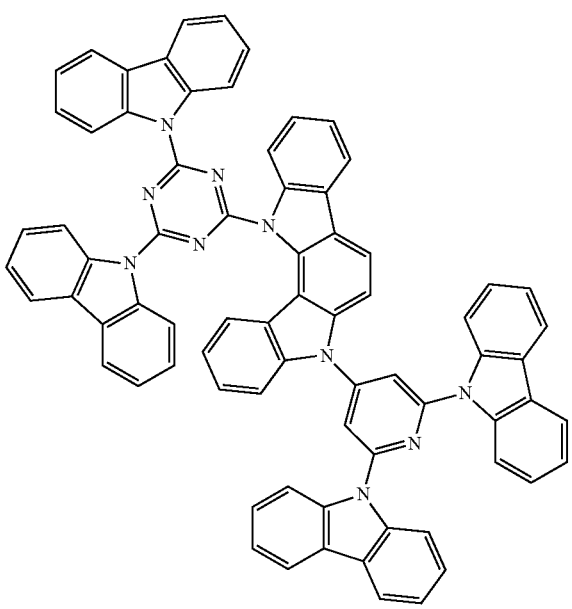

70
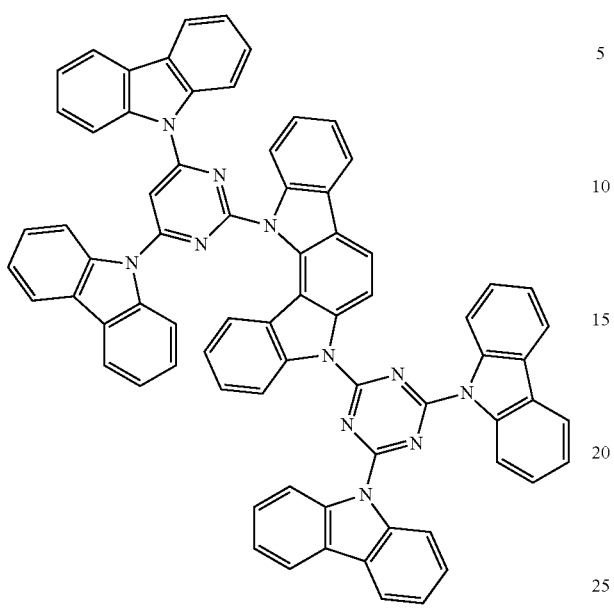
71
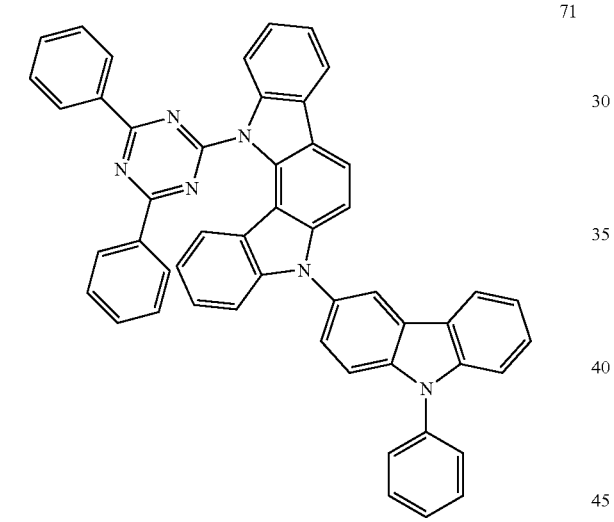
72
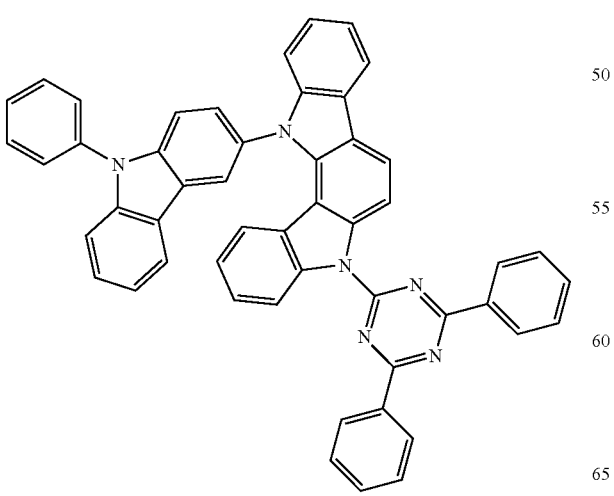
73
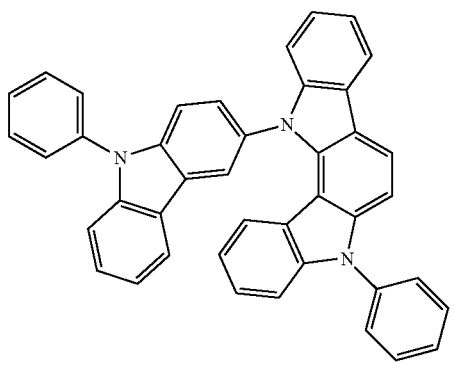
74
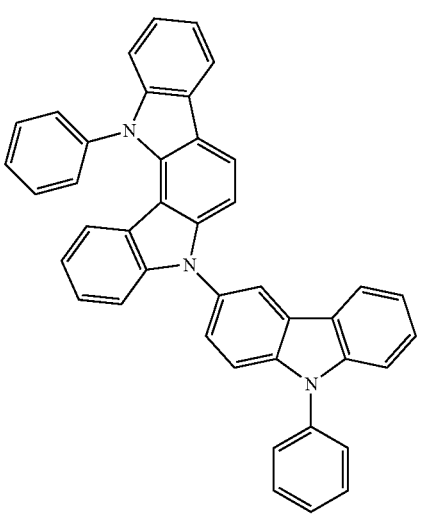
75
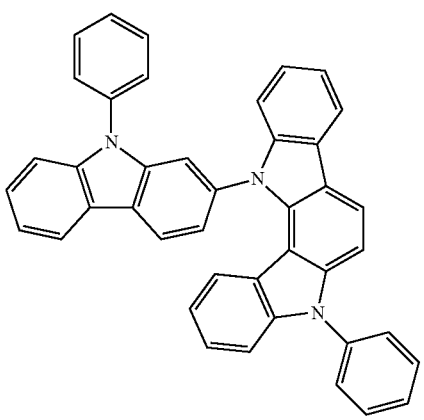

76
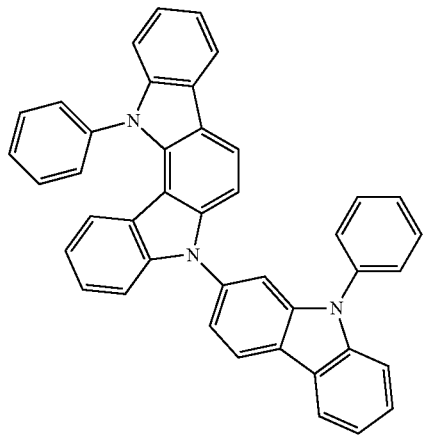
77
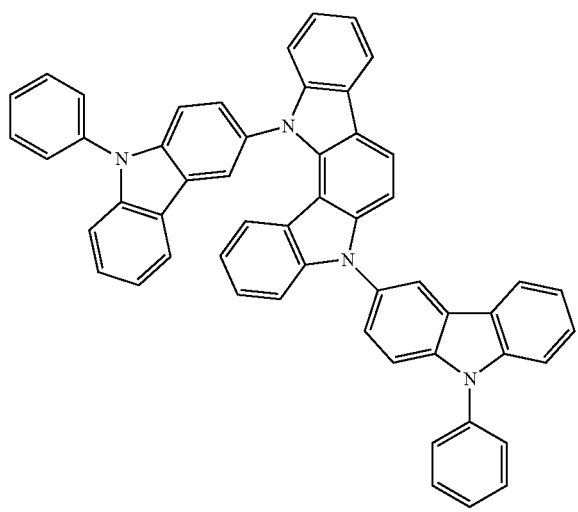
78
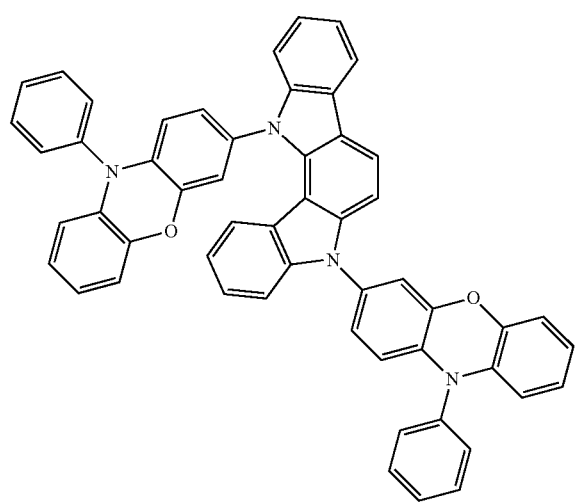
79
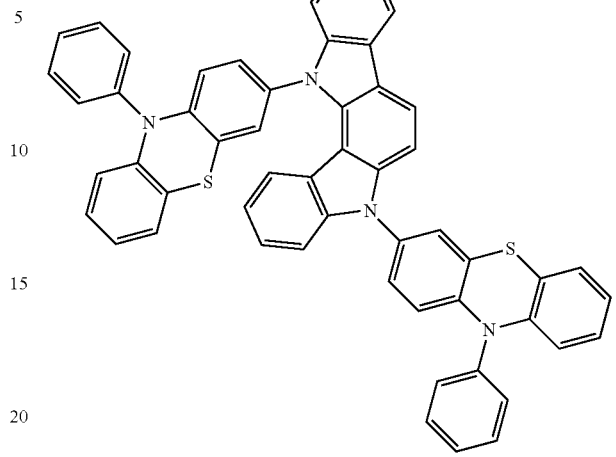
80
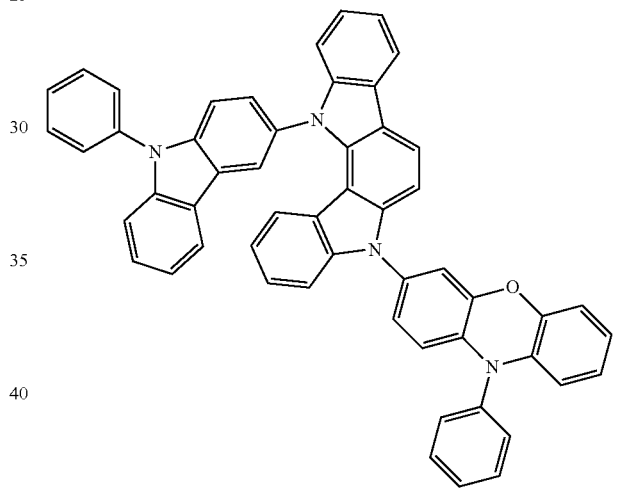
81
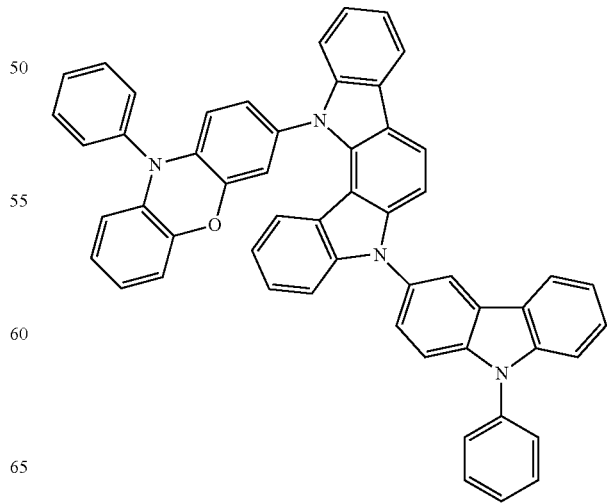

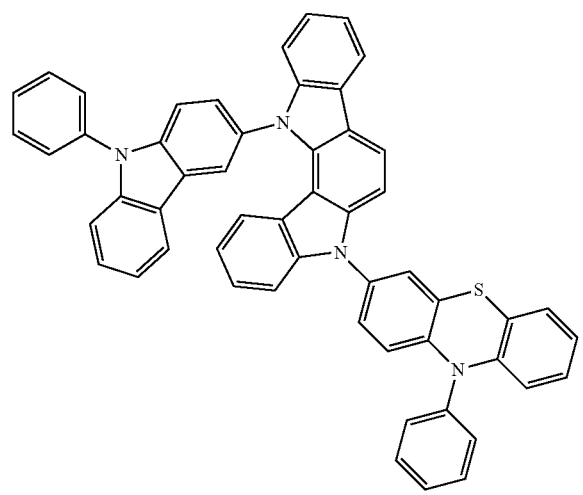
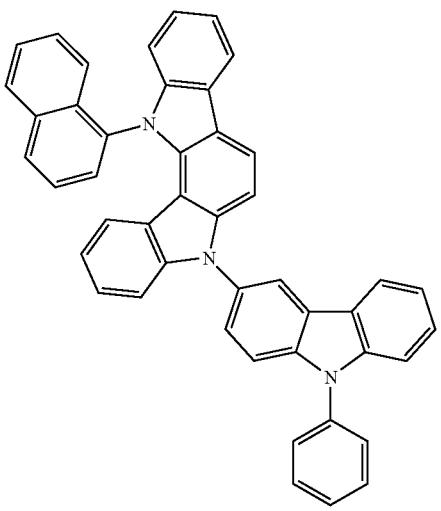

88
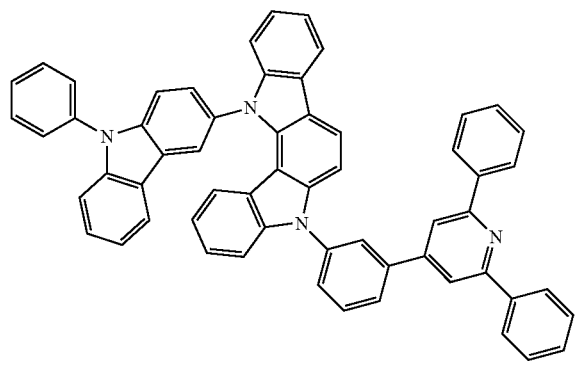
89
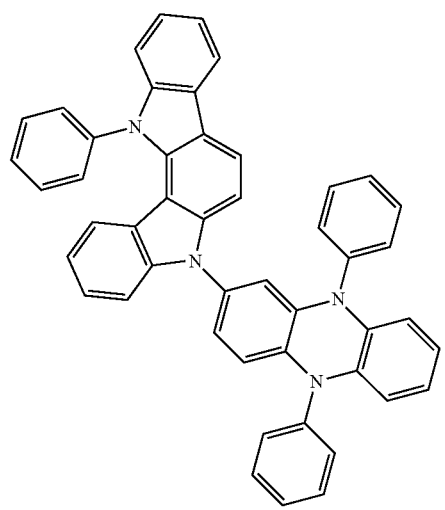
90
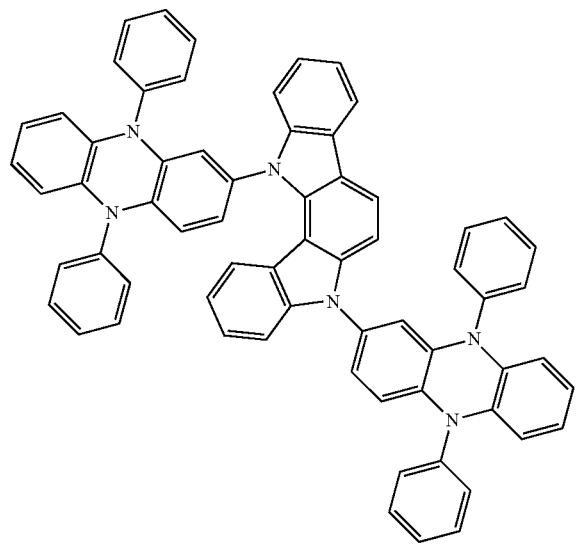
91
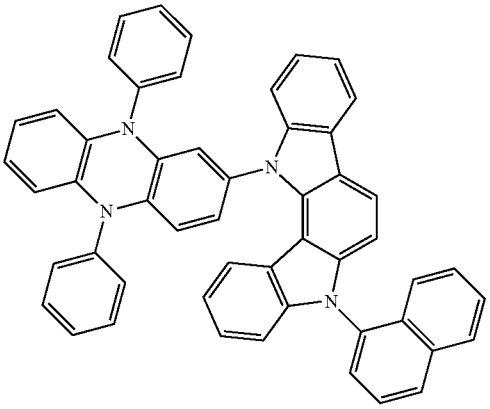
92
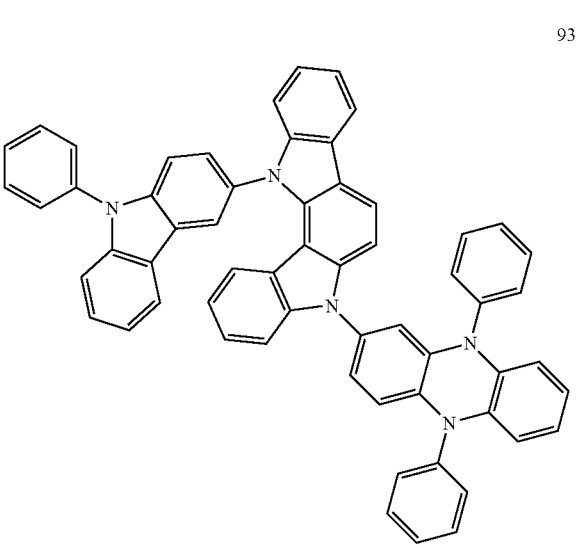
93

94

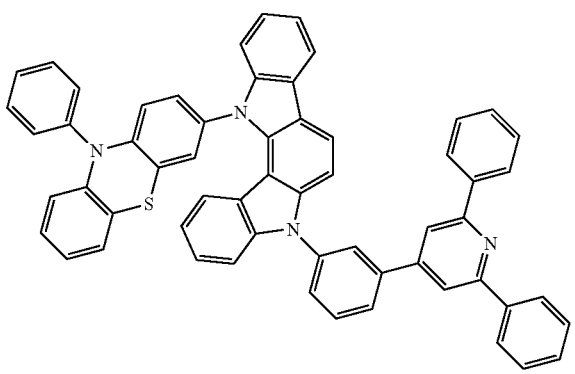

95

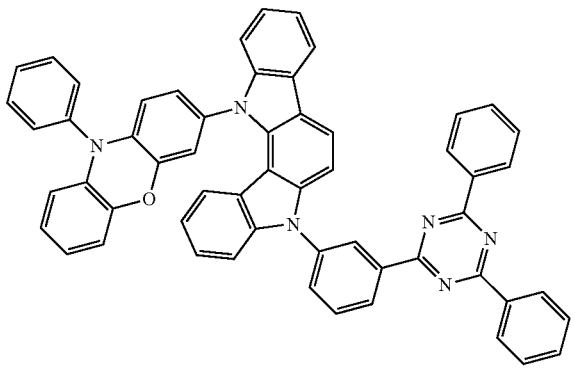

96

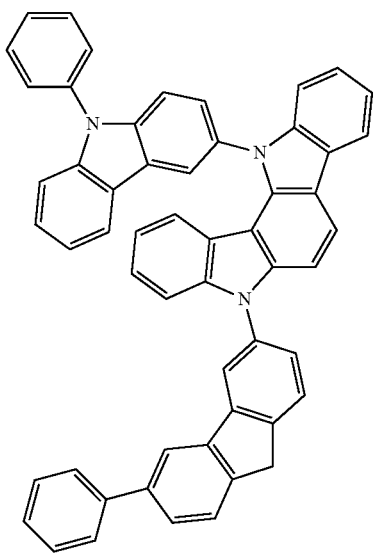

97

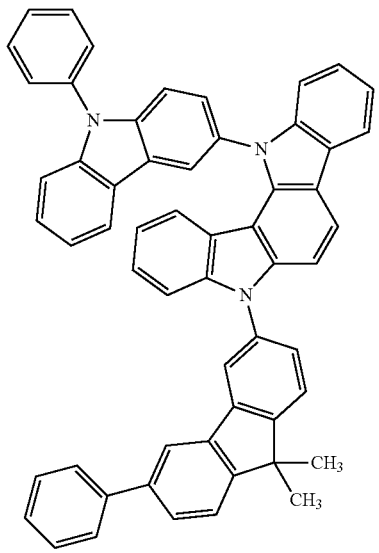

98

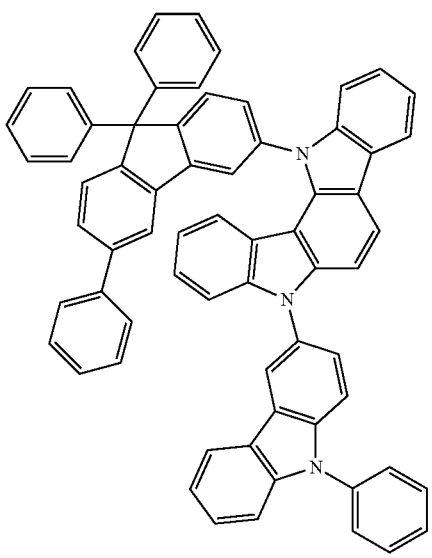

When the material for a phosphorescent light-emitting device of the present invention is contained in organic layers in an organic EL device formed by laminating an anode, the organic layers, and a cathode on a substrate, an excellent organic electroluminescent device is provided. A light-emitting layer, a hole-transporting layer, an electron-transporting layer, and a hole-blocking layer are suitable as the organic layers in which the material for a phosphorescent light-emitting device is contained. It is more preferred that the material for a phosphorescent light-emitting device be contained in the light-emitting layer, and it is still more preferred that the material for a phosphorescent light-emitting device be contained as a host material in a light-emitting layer containing a phosphorescent light-emitting dopant.

Next, the organic EL device using the material for a phosphorescent light-emitting device of the present invention is described.

The organic EL device of the present invention has a plurality of organic layers between an anode and a cathode laminated on a substrate. At least one of the plurality of organic layers is a light-emitting layer emitting phosphorescent light, and at least one of the organic layers is a layer containing the material for a phosphorescent light-emitting device of the present invention. The material for a phosphorescent light-emitting device of the present invention is advantageously contained in the light-emitting layer. The material for a phosphorescent light-emitting device of the present invention is more advantageously contained in the light-emitting layer together with a phosphorescent light-emitting dopant.

Next, the structure of the organic EL device of the present invention is described with reference to the drawings. However, the structure of the organic EL device of the present invention is by no means limited to one shown in the drawings.

FIG. 1 is a cross-sectional view schematically showing a structural example of a general organic EL device used in the present invention. Reference numeral 1 denotes a substrate, 2 denotes an anode, 3 denotes a hole-injecting layer, 4 denotes a hole-transporting layer, 5 denotes a light-emitting layer, 6 denotes an electron-transporting layer, and 7 denotes a cathode. The organic EL device of the present invention may have an exciton-blocking layer adjacent to the light-emitting layer, or may have an electron-blocking layer between the light-emitting layer and the hole-injecting layer. The exciton-blocking layer can be inserted on any of the anode side and the cathode side of the light-emitting layer, and can also be inserted simultaneously at both sides. The organic EL device of the present invention has the substrate, the anode, the light-emitting layer, and the cathode as its essential layers. The organic EL device of the present invention preferably has a hole-injecting/transporting layer and an electron-injecting/transporting layer in addition to the essential layers, and more preferably has a hole-blocking layer between the light-emitting layer and the electron-injecting/transporting layer. Note that the hole-injecting/transporting layer means any one or both of the hole-injecting layer and the hole-transporting layer, and that the electron-injecting/transporting layer means any one or both of an electron-injecting layer and the electron-transporting layer.

Note that it is possible to adopt a reverse structure compared with FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers can be added or eliminated if necessary.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like can be used.

—Anode—

Preferably used as the anode in the organic EL device is an anode formed by using, as an electrode substance, any of a metal, an alloy, an electrically conductive compound, and a mixture thereof, all of which have a larger work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which can be used for manufacturing an amorphous, transparent conductive film. In order to produce the anode, it may be possible to form any of those electrode substances into a thin film by using a method such as vapor deposition or sputtering and form a pattern having a desired design thereon by photolithography. Alternatively, in the case of not requiring high pattern accuracy (about 100 μm or more), a pattern may be formed via a mask having a desired design when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred Ω/□ or less. Further, the thickness of the resultant film is, depending on the material used, selected from usually the range of 10 to 1,000 nm, preferably the range of 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a smaller work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode can be produced by forming any of those electrode substances into a thin film by using a method such as vapor deposition or sputtering. Further, the sheet resistance as the cathode is preferably several hundred Ω/□ or less, and the thickness of the resultant film is selected from usually the range of 10 nm to 5 μm, preferably the range of 50 to 200 nm. Note that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer is a phosphorescent light-emitting layer and includes a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold. Such organic metal complexes are known in the prior art documents and the like, and a complex is selected therefrom and can be used.

Preferred examples of the phosphorescent light-emitting dopant include complexes such as Ir(ppy)3, complexes such as Ir(bt)2.acac3, and complexes such as PtOEt3, the complexes each having a noble metal element such as Ir as a central metal. Specific examples of those complexes are shown below, but the complexes are not limited to the compounds described below.

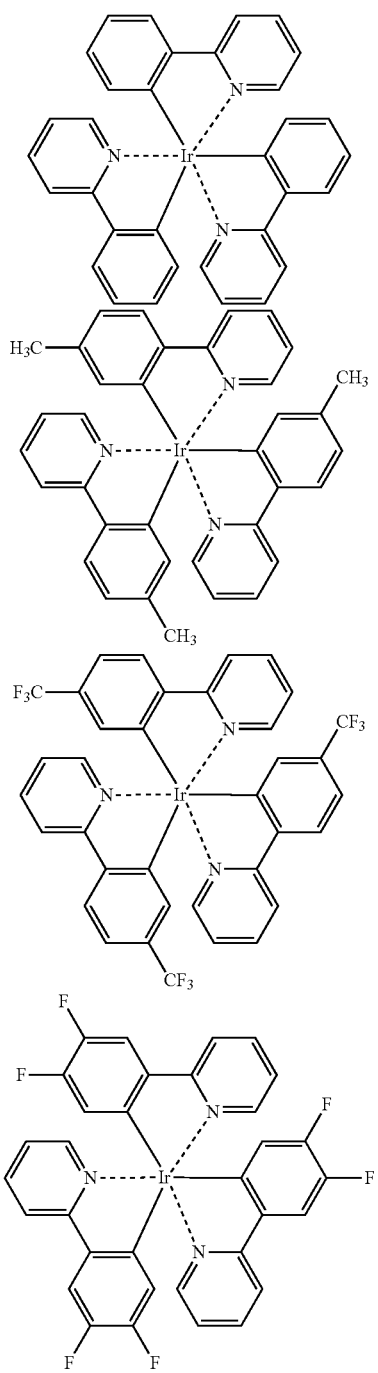

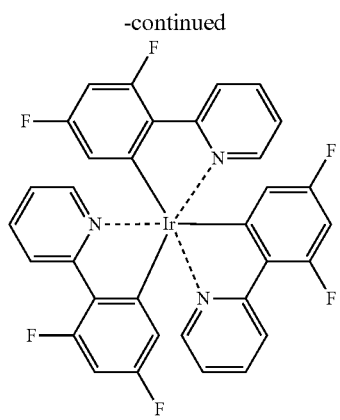

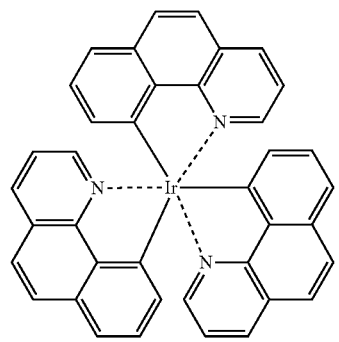

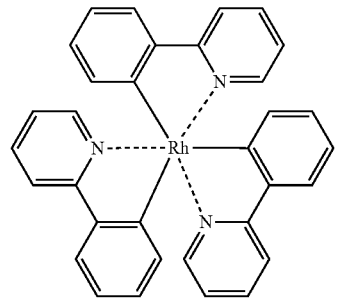

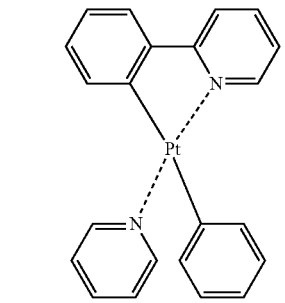

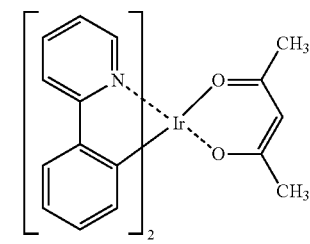

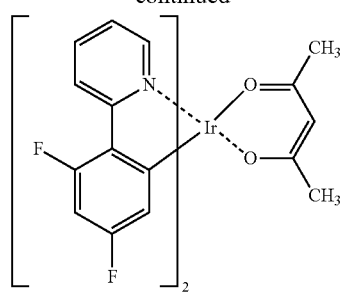
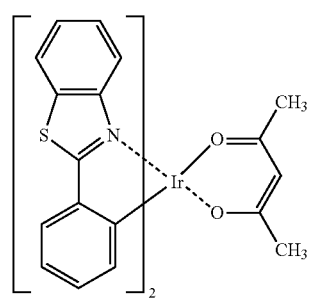
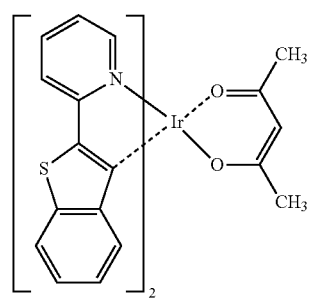
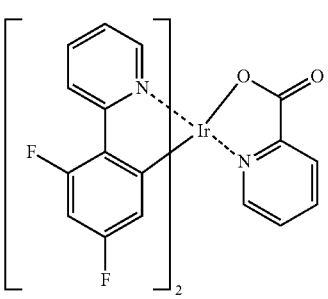
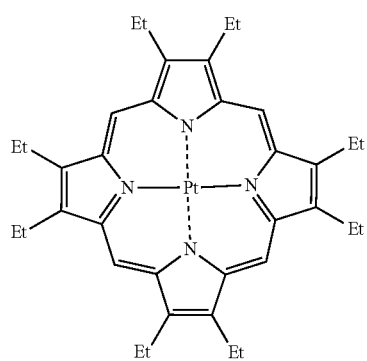
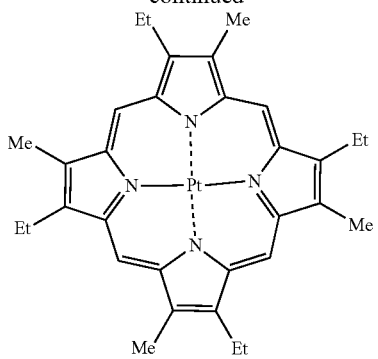
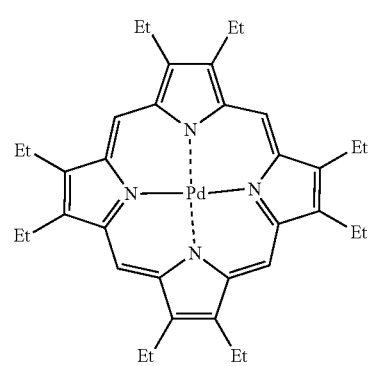
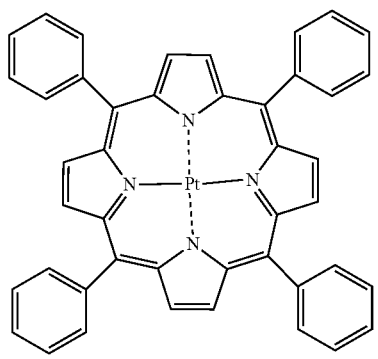
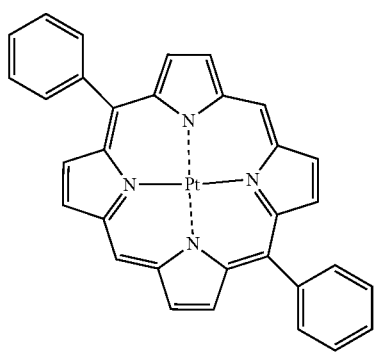

-continued

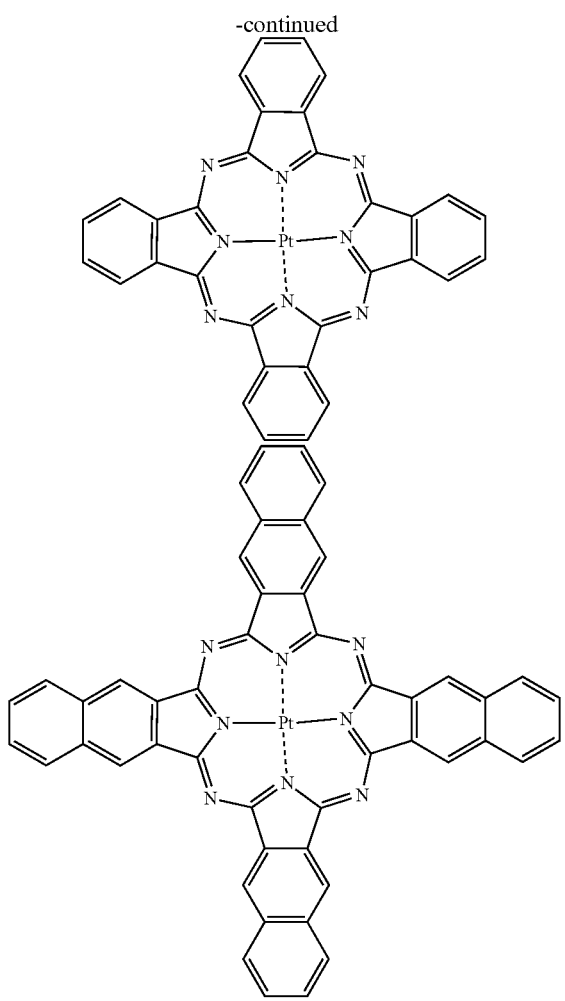

The content of the phosphorescent light-emitting dopant in the light-emitting layer is in the range of preferably 1 to 50 wt %, more preferably 5 to 30 wt %.

It is preferred to use, as a host material in the light-emitting layer, an indolocarbazole compound represented by the general formula (1) according to the present invention. However, when the indolocarbazole compound is used in any of the organic layers other than the light-emitting layer, the host material to be used in the light-emitting layer may be another host material other than the indolocarbazole compound, or the indolocarbazole compound and any other host material may be used in combination. Further, a plurality of kinds of known host materials may be used in combination.

It is preferred to use, as a usable known host compound, a compound that has a hole-transporting ability and an electron-transporting ability, is capable of preventing luminescence from having a longer wavelength, and has a higher glass transition temperature.

Such other host materials are known because they are mentioned in many patent literatures and the like, and hence a suitable host material can be chosen from those in the patent literatures and the like. Specific examples of the host material, which are not particularly limited, include an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrine-based compound, an anthraquinodimethane derivative, an anthrone derivative, a diphenylquinone derivative, a thiopyrane dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a polyphenylene derivative, a polyphenylene vinylene derivative, and a polyfluorene derivative.

—Injecting Layer—

The injecting layer refers to a layer provided between an electrode and an organic layer for the purpose of lowering a driving voltage and improving a light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer can be provided as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use an indolocarbazole compound represented by the general formula (1) according to the present invention for the hole-blocking layer. However, when the indolocarbazole compound is used in any of the organic layers other than the hole-blocking layer, a known material for a hole-blocking layer may be used. Further, it is possible to use, as a material for the hole-blocking layer, any of the below-mentioned materials for the electron-transporting layer if necessary.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

It is possible to use, as a material for the electron-blocking layer, any of the below-mentioned materials for the hole-transporting layer if necessary. The thickness of the electron-blocking layer is preferably 3 to 100 nm, more preferably 5 to 30 nm.

—Exciton-Blocking Layer—

The exciton-blocking layer refers to a layer used for blocking excitons produced by the recombination of a hole and an electron in the light-emitting layer from diffusing in charge-transporting layers. Inserting this layer enables effective confinement of the excitons in the light-emitting layer, thereby being able to improve the light-emitting efficiency of the device. The exciton-blocking layer can be inserted on any of the anode side and the cathode side of the adjacent light-emitting layer, and can also be inserted simultaneously at both sides.

A material for the exciton-blocking layer is exemplified by 1,3-dicarbazolylbenzene (mCP) and bis(2-methyl-8-quinolinolato)-4-phenylphenolatoaluminum (III) (BAlq).

—Hole-Transporting Layer—

The hole-transporting layer is formed of a hole-transporting material having a function of transporting holes, and a single hole-transporting layer or a plurality of hole-transporting layers can be provided.

The hole-transporting material has hole-injecting property or hole-transporting property or has electron-blocking property, and any of an organic compound and an inorganic compound may be used as the hole-transporting material. It is preferred to use an indolocarbazole compound represented by the general formula (1) according to the present invention for the hole-transporting layer. However, it is possible to select and use any compound from conventionally known compounds. Examples of the known hole-transporting material which can be used include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive polymeric oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers can be provided.

It is recommended that an electron-transporting material (which also serves as a hole-blocking material in some cases) have a function of transferring electrons injected from the cathode into the light-emitting layer. It is preferred to use an indolocarbazole compound represented by the general formula (1) according to the present invention for the electron-transporting layer. However, it is possible to select and use any compound from conventionally known compounds. Examples thereof include a nitro-substituted fluorene derivative, a diphenylquinone derivative, a thiopyran dioxide derivative, carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the above-mentioned oxadiazole derivative and a quinoxaline derivative which has a quinoxaline ring known as an electron withdrawing group. Further, it is also possible to use a polymer material in which any of those materials is introduced in a polymer chain or is used as a polymer main chain.

EXAMPLES

Hereinafter, the present invention is described in more detail with reference to examples, and the present invention is, as a matter of course, not limited to these examples. The present invention can be carried out in various forms as long as the various forms do not deviate from the gist of the present invention.

The routes described below were used to synthesize indolocarbazole compounds each serving as a material for a phosphorescent light-emitting device. Note that the number of each compound corresponds to the number given to each chemical formula described above.

Synthesis Example 1

Synthesis of 5,12-dihydroindolo[3,2-a]carbazole (IC)

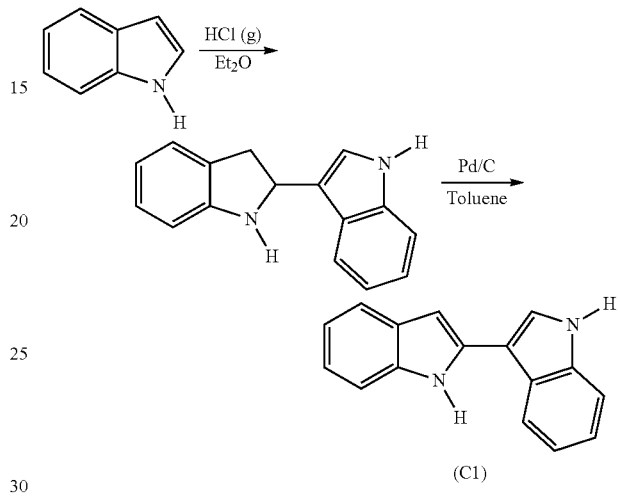

Under a nitrogen atmosphere, a hydrogen chloride gas produced by dropping 112.0 g (1.10 mol) of concentrated hydrochloric acid to 211.7 g (2.16 mol) of concentrated sulfuric acid over 1 hour was blown into a solution of 20.0 g (0.17 mol) of indole in 300 ml of dry diethyl ether, while the solution was being stirred at room temperature. After the reaction solution was stirred at room temperature for 15 hours, 121.0 g of ethyl acetate and 303.2 g of a saturated sodium hydrogen carbonate aqueous solution were added. After the aqueous layer in the mixture was extracted with ethyl acetate (2×100 ml), the organic layer was washed with a saturated sodium hydrogen carbonate aqueous solution (100 ml) and distilled water (2×100 ml). The organic layer was dried with anhydrous magnesium sulfate, followed by filtration of magnesium sulfate and vacuum distillation of the solvent. The resultant residue was dissolved in 150 ml of toluene, and 2.5 g of palladium/activated carbon were added. Then, the mixture was stirred for 3 hours while being heated at 111° C. to reflux. The reaction solution was cooled to room temperature, followed by filtration of the palladium/activated carbon and vacuum distillation of the solvent. The resultant was purified by recrystallization, yielding 14.7 g (yield 37%) of an intermediate (C1) as a white crystal.

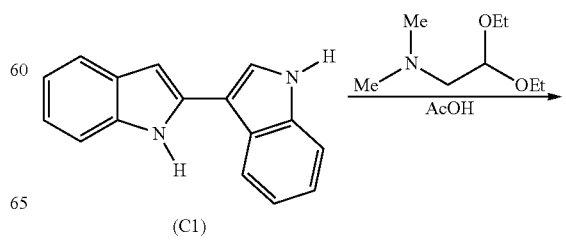

-continued

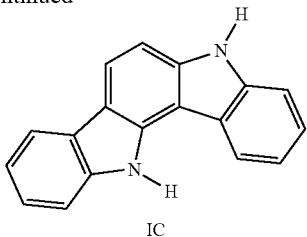

IC

Under a nitrogen atmosphere, 14.1 g (0.061 mol) of the intermediate (C1), 11.4 g (0.071 mol) of N,N-dimethylaminoacetaldehyde diethyl acetal, and 110.0 g of acetic acid were stirred for 8 hours while being heated at 118° C. to reflux. After the reaction solution was cooled to room temperature, the precipitated crystal was filtrated, followed by washing with acetic acid (30 ml). The resultant crystal was subjected to purification by reslurrying, yielding 10.4 g (yield 67%) of IC as a white crystal.

Example 1

Synthesis of Compound 34

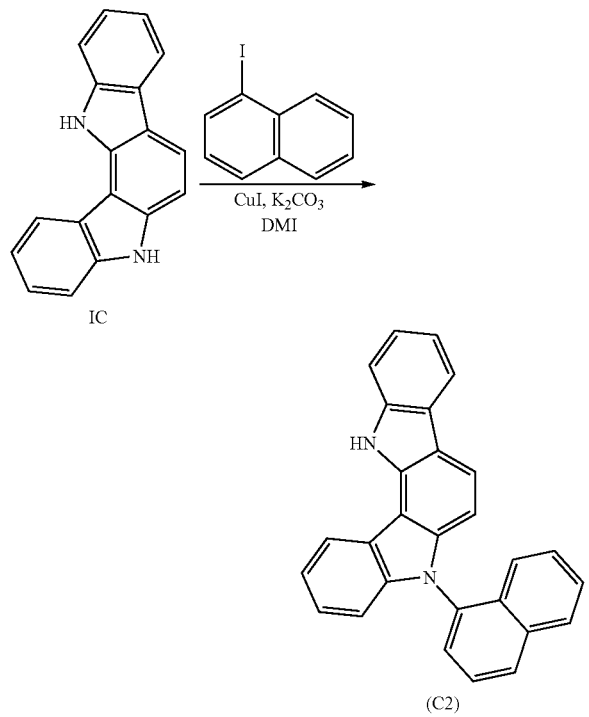

Under a nitrogen atmosphere, 73.3 g (0.29 mol) of IC, 87.8 g (0.35 mol) of 1-iodonaphthalene, 18.6 g (0.098 mol) of copper iodide, 154.8 g (1.1 mol) of potassium carbonate, and 800.0 g of 1,3-dimethyl-2-imidazolidinone were added and the mixture was stirred. After that, the mixture was heated to 190° C. and stirred for 120 hours. The reaction solution was cooled to room temperature, followed by filtration of inorganic compounds. The filtrate was added to 3,000 ml of water and the mixture was stirred, followed by filtration of the precipitated crystal. The crystal was subjected to drying under reduced pressure and was then purified by column chromatography, yielding 43.8 g (0.11 mol, yield 40%) of an intermediate (C2) as a white powder.

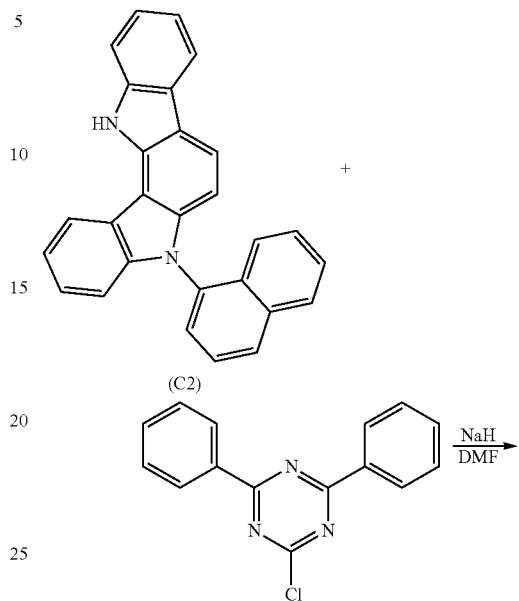

Under a nitrogen atmosphere, 1.7 g (0.041 mol) of 56.4% sodium hydride and 50 ml of dry N,N-dimethylformamide (DMF) were added and the mixture was stirred. 50 ml of dry DMF were added to 10.0 g (0.026 mol) of the intermediate C2 produced as described above to prepare a solution, and the resultant solution was dropped over 10 minutes. After completion of the dropping, the mixture was continuously stirred at room temperature for 1 hour. Then, 50 ml of dry DMF were added to 7.4 g (0.027 mol) of 2-chloro-4,6-diphenyl-1,3,5-triazine to prepare a solution, and the resultant solution was dropped over 1 hour. After completion of the dropping, the mixture was continuously stirred for 3 hours. After that, 300 ml of water were added, followed by filtration of the precipitated crystal. The filtrated crystal was subjected to drying under reduced pressure, followed by reslurrying under heat with methanol twice. The resultant crystal was subjected to drying under reduced pressure and was then purified by column chromatography, yielding 3.0 g (0.0049 mol, yield 19%) of Compound 34 as a slightly yellow powder.

Figure 2:
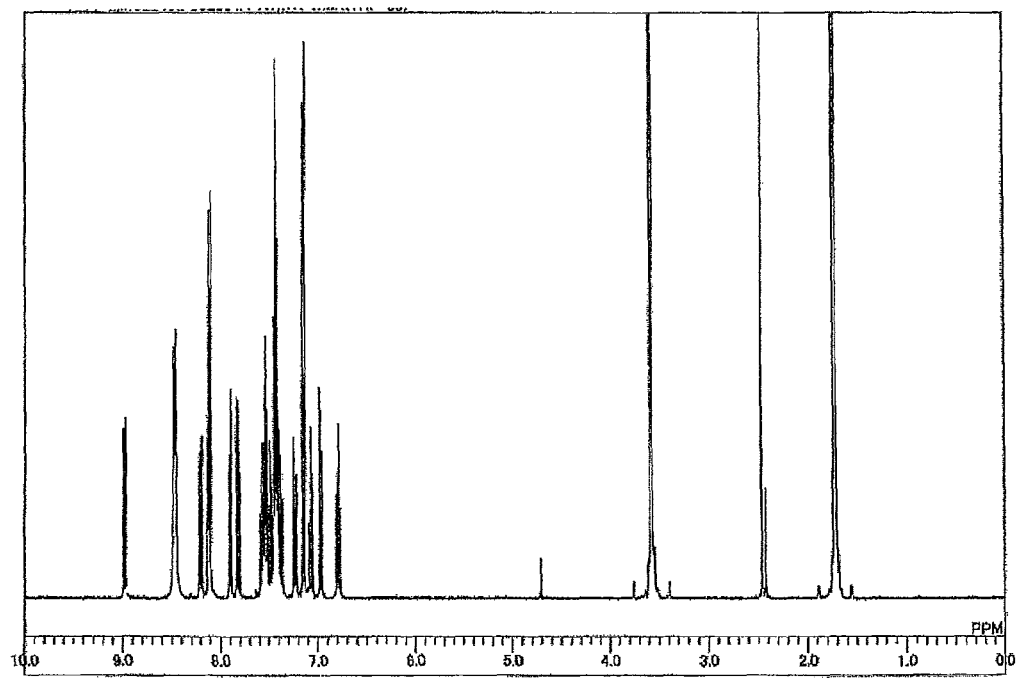
FIG. 2 shows a $^1$H-NMR chart of an indolocarbazole compound 34 of the present invention.

APCI-TOFMS: m/z 614 [M+H]+. FIG. 2 shows ¹H-NMR measurement results (measurement solvent: THF-d8).

Example 2

Synthesis of Compound 36

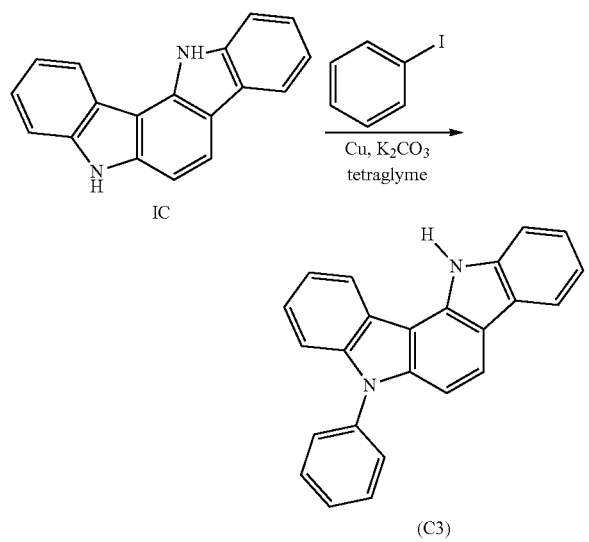

(C3)

Under a nitrogen atmosphere, 10.0 g (0.039 mol) of IC, 39.8 g (0.20 mol) of iodobenzene, 6.2 g (0.098 mol) of copper, 8.1 g (0.059 mol) of potassium carbonate, and 200 ml of tetraglyme were added and the mixture was stirred. The mixture was then heated to 190° C. and stirred for 24 hours. The reaction solution was cooled to room temperature, followed by filtration of copper and inorganic compounds. 200 ml of distilled water were added to the filtrate and the mixture was stirred, followed by filtration of the precipitated crystal. The crystal was subjected to drying under reduced pressure and was then purified by column chromatography, yielding 9.7 g (0.029 mol, yield 75.0%) of an intermediate (C3) as a white powder.

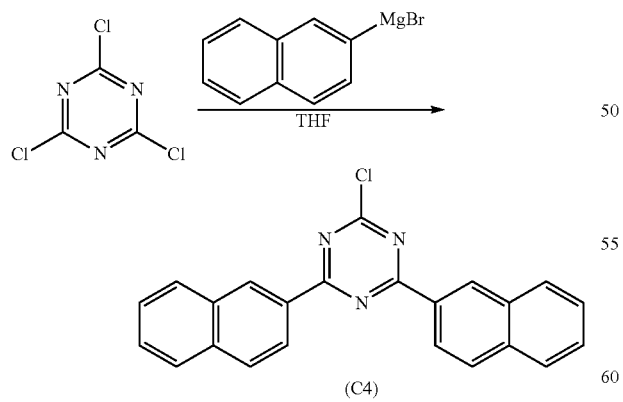

(C4)

Under a nitrogen atmosphere, 10 g of dry tetrahydrofuran (THF) were added to 3.65 g (0.15 mol) of magnesium, followed by stirring. 0.05 g (0.0040 mol) of iodine was added to the mixture, followed by heating to 70° C. While the mixture was kept at 70° C., a solution prepared by dissolving 32.1 g (0.155 mol) of 2-bromonaphthalene in 100.0 g of dry THF was dropped therein over 1 hour, followed by reflux for 2 hours. Then, the resultant mixture was cooled in an ice bath so as to have an inner temperature of 3° C. Then, a solution prepared by dissolving 9.2 g (0.050 mol) of cyanuric chloride in 50.0 g of THF was dropped in the mixture over 30 minutes while the inner temperature of the solution was kept at 15° C. or less, followed by stirring for 5 hours. The inner temperature of the resultant mixture was lowered again to 5° C. in an ice bath, and 50 g (0.16 mol) of a 10% hydrochloric acid solution were dropped therein over 10 minutes, followed by addition of 150 g of toluene and stirring. Then, the mixture was transferred to a separating funnel, and the resultant organic layer was washed with distilled water (3×50 g). The obtained organic layer was concentrated to dryness. After that, 75.0 g of THF were added thereto to dissolve the residue, followed by addition of 200.0 g of methanol. Reslurrying was carried out for 1 hour, followed by filtration of a white crystal. The crystal was subjected to purification by reslurrying, followed by drying under reduced pressure, yielding 11.0 g (0.030 mol) of an intermediate (C4) as a white powder.

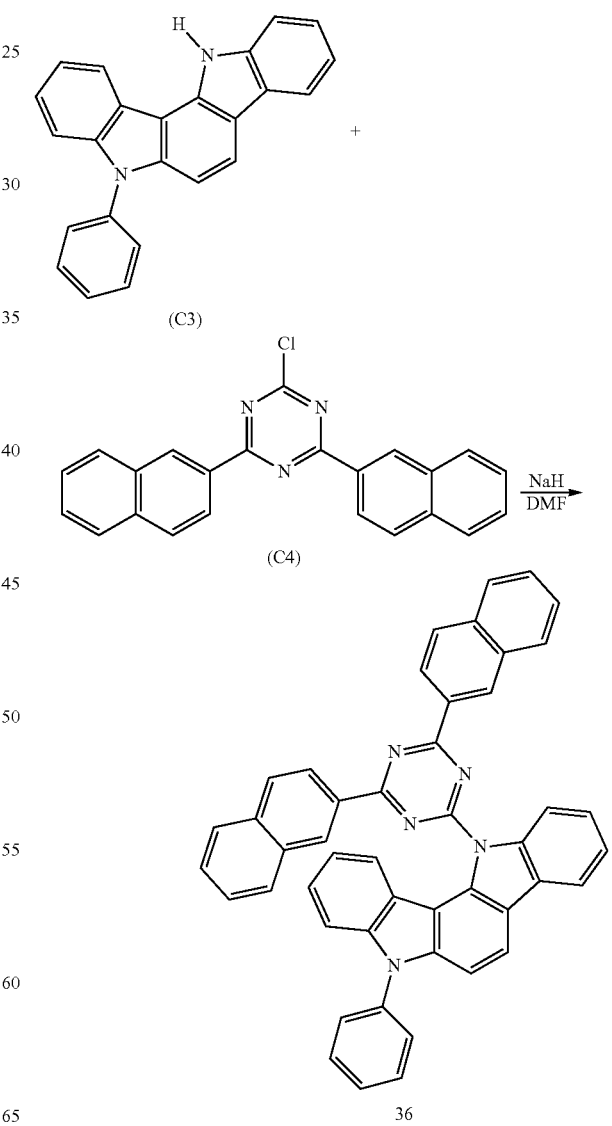

36

Figure 3:
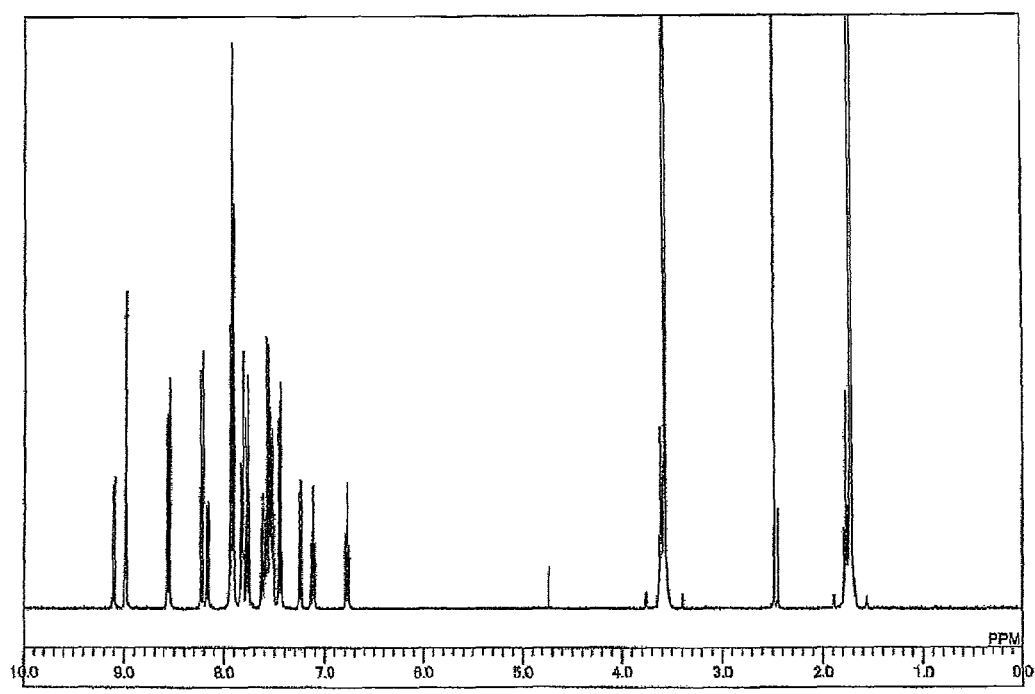
FIG. 3 shows a $^1$H-NMR chart of an indolocarbazole compound 36 of the present invention.

Under a nitrogen atmosphere, 1.0 g (0.025 mol) of 60.8% sodium hydride and 10.0 g of dry N,N-dimethylformamide (DMF) were added in a flask and the mixture was stirred. A solution prepared by dissolving 6.45 g (0.019 mol) of the intermediate (C3) yielded as describe above in 10.0 g of DMF was dropped into the flask over 10 minutes, followed by stirring for 1 hour. After that, a solution prepared by dissolving 7.00 g (0.019 mol) of the intermediate (C4) in 10.0 g of DMF was dropped therein over 10 minutes, followed by stirring for 7 hours. Then, 4.0 g of distilled water were added and 100.0 g of methanol were added, followed by filtration of the precipitated crystal. The crystal was subjected to drying under reduced pressure and was then purified by column chromatography, yielding 9.5 g (0.014 mol, yield 75%) of Compound 36 as a white powder. Melting points: 274° C. and 287° C., APCI-TOFMS: m/z 664 [M+H]$^+$. FIG. 3 shows $^1$H-NMR measurement results (measurement solvent: THF-d8).

Compounds 22, 33, 49, 71, 72, 77, 78, 81, and 87 were synthesized according to the above-mentioned synthesis examples, and they were used for manufacturing organic EL devices.

Example 3

On a glass substrate on which ITO had been formed into an anode having a film thickness of 150 nm, each thin film was laminated by using a vacuum deposition method at a vacuum degree of $4.0 \times 10^{-4}$ Pa. First, on the ITO film, copper phthalocyanine (CuPc) was formed into a film having a thickness of 25 nm as a hole-injecting layer. Next, on the hole-injecting layer, 4,4'-bis[N-(1-naphthyl)-N-phenylamino]biphenyl (NPB) was formed into a film having a thickness of 55 nm as a hole-transporting layer. Next, on the hole-transporting layer, co-vapor deposition was carried out by using Compound 34 as a host component and bis(2-(2'-benzo[4,5-a]thienyl)pyridinato-N,C3) iridium(acetylacetonate)[(Btp)$_2$Iracac] as a guest component from different vapor deposition sources, forming a light-emitting layer having a thickness of 47.5 nm. In this case, the concentration of (Btp)$_2$Iracac was 8.0 wt %. Next, tris(8-hydroxyquinolinato) aluminum (III) (Alq3) was formed into a film having a thickness of 30 nm as an electron-transporting layer. Further, on the electron-transporting layer, lithium fluoride (LiF) was formed into a film having a thickness of 1 nm as an electron-injecting layer. Finally, on the electron-injecting layer, aluminum (Al) was formed into a film having a thickness of 200 nm as an electrode. As a result, an organic EL device was provided.

An external power source was connected to the resultant organic EL device, followed by application of a DC voltage. As a result, the organic EL device was found to have the luminescence properties shown in Table 1. In Table 1, the values of luminance, voltage, and luminous efficiency are those at 10 mA/cm$^2$. Note that the maximum wavelength of the luminescence spectrum of the device is 620 nm, showing that luminescence is provided by (Btp)$_2$Iracac.

Example 4

An organic EL device was manufactured in the same manner as that in Example 3 except that Compound 33 was used instead as the host component of the light-emitting layer.

Example 5

An organic EL device was manufactured in the same manner as that in Example 3 except that Compound 36 was used instead as the host component of the light-emitting layer.

Example 6

An organic EL device was manufactured in the same manner as that in Example 3 except that Compound 71 was used instead as the host component of the light-emitting layer.

Example 7

An organic EL device was manufactured in the same manner as that in Example 3 except that Compound 72 was used instead as the host component of the light-emitting layer.

Example 8

An organic EL device was manufactured in the same manner as that in Example 3 except that Compound 22 was used instead as the host component of the light-emitting layer.

Example 9

An organic EL device was manufactured in the same manner as that in Example 3 except that Compound 49 was used instead as the host component of the light-emitting layer.

Example 10

An organic EL device was manufactured in the same manner as that in Example 3 except that Compound 87 was used instead as the host component of the light-emitting layer.

Comparative Example 1

An organic EL device was manufactured in the same manner as that in Example 3 except that bis(2-methyl-8-quinolinolato)-4-phenylphenolatoaluminum (BAlq) was used instead as the host component of the light-emitting layer.

Comparative Example 2

An organic EL device was manufactured in the same manner as that in Example 3 except that Compound C below was used instead as the host component of the light-emitting layer.

(C)

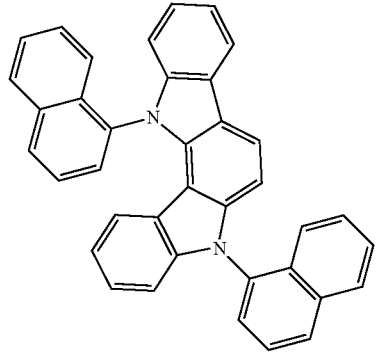

The maximum wavelength of the luminescence spectrum of the device obtained in each of Examples 3 to 8 and Comparative Examples 1 and 2 is 620 nm, showing that luminescence is provided by (Btp)$_2$Iracac Table 1 shows the luminescence properties of each device.

TABLE 1

| | Host component | Luminescence properties (@10 mA/cm$^2$) | | |
|---|---|---|---|---|
| | | Luminance (cd/m$^2$) | Voltage (V) | Visual luminous efficiency (lm/W) |
| Example 3 | Compound 34 | 1390 | 6.2 | 7.0 |
| Example 4 | Compound 33 | 1370 | 6.3 | 6.8 |
| Example 5 | Compound 36 | 1240 | 6.4 | 6.1 |
| Example 6 | Compound 71 | 1420 | 6.5 | 6.9 |
| Example 7 | Compound 72 | 1410 | 6.6 | 6.7 |
| Example 8 | Compound 22 | 1430 | 6.7 | 6.8 |
| Example 9 | Compound 49 | 1480 | 6.8 | 6.8 |
| Example 10 | Compound 87 | 1260 | 7.2 | 5.5 |
| Comp. Ex. 1 | BAlq | 1020 | 8.4 | 3.8 |
| Comp. Ex. 2 | Compound C | 1070 | 7.9 | 4.1 |

Example 11

On a glass substrate on which ITO had been formed into an anode having a film thickness of 150 nm, each thin film was laminated by using a vacuum deposition method at a vacuum degree of 4.0×10$^{-4}$ Pa. First, on the ITO film, CuPc was formed into a film having a thickness of 25 nm as a hole-injecting layer. Next, Compound 77 was formed into a film having a thickness of 30 nm as a hole-transporting layer. Next, on the hole-transporting layer, co-vapor deposition was carried out by using 2,6-di(4-carbazolylphenyl)pyridine and Ir(PPy)$_3$ from different vapor deposition sources, forming a light-emitting layer having a thickness of 40 nm. In this case, the concentration of Ir(PPy)$_3$ was 6.0 wt %. Next, Alq3 was formed into a film having a thickness of 20 nm as an electron-transporting layer. Further, on the electron-transporting layer, lithium fluoride (LiF) was formed into a film having a thickness of 0.5 nm as an electron-injecting layer. Finally, on the electron-injecting layer, aluminum (Al) was formed into a film having a thickness of 170 nm as an electrode. As a result, an organic EL device was provided.

An external power source was connected to the resultant organic EL device, followed by application of a DC voltage. As a result, the organic EL device was found to have the luminescence properties shown in Table 1. In Table 1, the values of luminance, voltage, and luminous efficiency are those at the time of driving each device at 2.5 mA/cm$^2$. Further, the half-life time of luminance is shown by the value obtained by evaluating the device based on constant current drive at 20 mA/cm$^2$, and converting the results of the evaluation to the case of an initial luminance of 1,000 cd/m$^2$. The maximum wavelength of the luminescence spectrum of the device is 517 nm, showing that luminescence is provided by Ir(PPy)$_3$.

Example 12

An organic EL device was manufactured in the same manner as that in Example 11 except that Compound 78 was used instead as the hole-transporting layer material.

Example 13

An organic EL device was manufactured in the same manner as that in Example 11 except that Compound 81 was used instead as the hole-transporting layer material.

Comparative Example 3

An organic EL device was manufactured in the same manner as that in Example 11 except that NPB was used instead as the hole-transporting layer material.

The maximum wavelength of the luminescence spectrum of the device obtained in each of Examples 11 to 13 and Comparative Example 3 is 517 nm, showing that luminescence is provided by Ir(PPy)$_3$. Table 2 shows the luminescence properties of each device.

TABLE 2

| | Hole-transporting layer material | Luminescence properties (@2.5 mA/cm$^2$) | | |
|---|---|---|---|---|
| | | Luminance (cd/m$^2$) | Voltage (V) | Visual luminous efficiency (lm/W) |
| Example 11 | Compound 77 | 1230 | 4.3 | 35.9 |
| Example 12 | Compound 78 | 1270 | 4.4 | 36.3 |
| Example 13 | Compound 81 | 1340 | 4.2 | 40.1 |
| Comp. Ex. 3 | NPB | 832 | 4.3 | 24.2 |

INDUSTRIAL APPLICABILITY

The material for a phosphorescent light-emitting device of the present invention has a high ability of injecting/transporting both charges, and hence, by using the material in an organic EL device, the driving voltage of the device lowers. Besides, when a light-emitting layer includes this material for a phosphorescent light-emitting device, the balance between both charges improves, and hence the probability of their recombination increases. Further, the material for a phosphorescent light-emitting device has energy in the minimum excited triplet state, the energy being sufficiently high to confine energy in the minimum excited triplet state of a dopant. Thus, the transfer of triplet excitation energy from the dopant to a host molecule can be effectively suppressed. By virtue of the above-mentioned respects, high luminous efficiency has been accomplished. In addition, the material for a phosphorescent light-emitting device exhibits a good amorphous characteristic and high thermal stability and has electrochemical stability, resulting in the achievement of an organic EL devise having a long operation life and having high durability.

The organic EL device according to the present invention has practically satisfactory levels in luminescence properties, operation life, and durability. Thus, the organic EL device has a large technical value in applications to flat panel displays (display devices for portable phones, in-vehicle display devices, display devices for OA computers, televisions, and the like), light sources exerting characteristics of planar light emitters (light sources in lighting equipment and copiers and backlight sources in liquid crystal displays and instruments), signboards, sign lamps, and the like.

The invention claimed is:

1. A material for a phosphorescent light-emitting device, said material comprising an indolocarbazole compound represented by the following general formula (1):

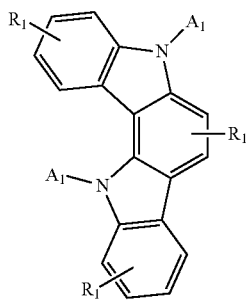

(1)

wherein in the formula (1):
each of $A_1$'s independently represents an aromatic hydrocarbon group having 6 to 50 carbon atoms, an aromatic heterocyclic group having 3 to 50 carbon atoms, an alkyl group having 1 to 10 carbon atoms, or a cycloalkyl group having 3 to 11 carbon atoms, provided that one or both of $A_1$'s represent an aromatic heterocyclic group represented by the following formula (1b) and represent no aromatic heterocyclic group represented by the following formula (1a); and each of $R_1$'s independently represents a hydrogen atom, an alkyl group having 1 to 10 carbon atoms, an alkoxy group having 1 to 6 carbon atoms, or an acyl group having 2 to 6 carbon atoms:

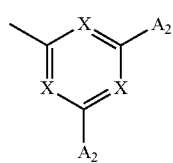

(1a)

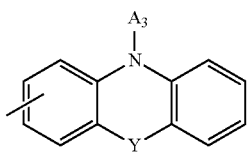

(1b)

wherein in the formula (1a), each of X's independently represents a methine group or a nitrogen atom, and at least one of X's in a ring including three X's represents a nitrogen atom;

wherein in the formula (1b), Y represents —$NA_4$- or —S—; and wherein in the formulae (1a) and (1b), $A_2$'s, $A_3$, and $A_4$ each independently represents an aromatic hydrocarbon group having 6 to 38 carbon atoms, an aromatic heterocyclic group having 3 to 37 carbon atoms, an alkyl group having 1 to 10 carbon atoms, or a cycloalkyl group having 3 to 11 carbon atoms.

2. An organic electroluminescent device, comprising an anode, a plurality of organic layers, and a cathode laminated on a substrate, wherein the organic electroluminescent device comprises an organic layer containing the material for a phosphorescent light-emitting device according to claim 1.

3. An organic electroluminescent device according to claim 2, wherein the organic layer containing the material for a phosphorescent light-emitting device comprises at least one layer selected from the group consisting of a light-emitting layer, a hole-transporting layer, an electron-transporting layer, and a hole-blocking layer.

4. An organic electroluminescent device according to claim 3, wherein the organic layer containing the material for a phosphorescent light-emitting device comprises a light-emitting layer containing a phosphorescent light-emitting dopant.

5. An organic electroluminescent device according to claim 3, wherein the organic layer containing the material for a phosphorescent light-emitting device comprises a hole-transporting layer.

6. The material for a phosphorescent light-emitting device according to claim 1, wherein both of $A_1$'s independently represent the aromatic heterocyclic group represented by formula (1b).

* * * * *